United States Patent
McNair

(10) Patent No.: US 12,361,951 B2
(45) Date of Patent: Jul. 15, 2025

(54) TOOL FOR ASSISTING PEOPLE WITH SPEECH DISORDER

(71) Applicant: Cerner Innovation, Inc., Kansas City, MO (US)

(72) Inventor: Douglas S. McNair, Seattle, WA (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

(21) Appl. No.: 18/199,594

(22) Filed: May 19, 2023

(65) Prior Publication Data

US 2023/0290353 A1    Sep. 14, 2023

Related U.S. Application Data

(63) Continuation of application No. 16/455,196, filed on Jun. 27, 2019, now Pat. No. 11,763,821.

(Continued)

(51) Int. Cl.
  *G10L 15/30*      (2013.01)
  *A61B 5/00*       (2006.01)
  (Continued)

(52) U.S. Cl.
  CPC ............. *G10L 15/30* (2013.01); *G10L 15/22* (2013.01); *G10L 25/54* (2013.01); *G10L 25/66* (2013.01);
  (Continued)

(58) Field of Classification Search
  CPC ......... G10L 15/00; G10L 15/20; G10L 15/22; G10L 15/26; G10L 15/30; G10L 25/00;
  (Continued)

(56) References Cited

U.S. PATENT DOCUMENTS 6,598,017 B1   7/2003   Yamamoto et al.
9,922,650 B1 * 3/2018   Secker-Walker ..... G10L 15/083
(Continued)

OTHER PUBLICATIONS

Fernando Martínez-Santiago, Arturo Montejo-Ráez, Miguel Á Garcia-Cumbreras, Pictogram Tablet: A Speech Generating Device Focused on Language Learning, Interacting with Computers, vol. 30, Issue 2, Mar. 2018, pp. 116-132, https://doi.org/10.1093/iwc/iwx022 (Year: 2018).*

(Continued)

*Primary Examiner* — Daniel C Washburn
*Assistant Examiner* — Sean E Serraguard
(74) *Attorney, Agent, or Firm* — Invoke

(57) ABSTRACT

Various tools are disclosed for providing assistive or augmentative means to enhance the fluency and accuracy of persons having speech disabilities. These technologies may automatically ascertain and dynamically improve the accuracy with which automatic speech recognition (ASR) systems recognize utterances of persons having impaired speech conditions. In an embodiment, digitized audio information about a speaker's utterance is processed to determine a set of candidate words matching the utterance. From these candidate words, a set of concepts is determined using a finite state machine model. A pictogram representing each concept is identified and presented to the speaker so that the speaker may select the pictogram corresponding to the best match of his or her intended meaning associated with the utterance. An action corresponding to speaker's selection then may be performed. For example, displaying or synthesizing speech from textual information describing the selected concept.

26 Claims, 15 Drawing Sheets

Related U.S. Application Data

(60) Provisional application No. 62/787,095, filed on Dec. 31, 2018, provisional application No. 62/690,943, filed on Jun. 27, 2018.

(51) Int. Cl.
    *G10L 15/20* (2006.01)
    *G10L 15/22* (2006.01)
    *G10L 15/26* (2006.01)
    *G10L 25/54* (2013.01)
    *G10L 25/63* (2013.01)
    *G10L 25/66* (2013.01)

(52) U.S. Cl.
    CPC .............. *A61B 5/4803* (2013.01); *G10L 15/20* (2013.01); *G10L 15/26* (2013.01); *G10L 25/63* (2013.01)

(58) Field of Classification Search
    CPC .......... G10L 25/54; G10L 25/63; G10L 25/66; A61B 5/00; A61B 5/4803
    See application file for complete search history.

(56) References Cited

U.S. PATENT DOCUMENTS

| | | | |
|---|---|---|---|
| 2004/0078190 A1 | 4/2004 | Fass et al. | |
| 2004/0111272 A1* | 6/2004 | Gao | G06F 40/58 704/277 |
| 2005/0017954 A1 | 1/2005 | Kay et al. | |
| 2006/0293893 A1 | 12/2006 | Horvitz | |
| 2008/0115090 A1 | 5/2008 | Disbrow | |
| 2008/0319750 A1 | 12/2008 | Potter et al. | |
| 2010/0222098 A1* | 9/2010 | Garg | H04M 1/72478 704/235 |
| 2010/0231752 A1 | 9/2010 | Lodge | |
| 2012/0265528 A1 | 10/2012 | Gruber et al. | |
| 2013/0211815 A1 | 8/2013 | Seligman et al. | |
| 2013/0239031 A1* | 9/2013 | Ubillos | H04N 1/387 715/810 |
| 2014/0136210 A1* | 5/2014 | Johnston | G10L 15/07 704/275 |
| 2015/0242117 A1 | 8/2015 | Nakashima | |
| 2016/0093291 A1 | 3/2016 | Kim | |
| 2016/0124615 A1 | 5/2016 | Jain et al. | |
| 2016/0148610 A1 | 5/2016 | Kennewick et al. | |
| 2017/0060854 A1* | 3/2017 | Zeng | G06F 40/30 |
| 2017/0103756 A1* | 4/2017 | Kobayashi | G10L 15/30 |
| 2017/0300462 A1* | 10/2017 | Cudworth | G06F 40/274 |
| 2017/0337191 A1* | 11/2017 | Narayanan | G06F 40/58 |
| 2018/0004729 A1 | 1/2018 | Qiu et al. | |
| 2018/0012593 A1 | 1/2018 | Prasad et al. | |
| 2018/0018144 A1 | 1/2018 | Morris et al. | |
| 2018/0174579 A1 | 6/2018 | Henry | |
| 2018/0190026 A1 | 7/2018 | Barnett et al. | |
| 2018/0358005 A1* | 12/2018 | Tomar | G06F 40/30 |
| 2019/0130904 A1 | 5/2019 | Homma et al. | |
| 2019/0318739 A1* | 10/2019 | Garg | G06F 3/167 |
| 2020/0020317 A1 | 1/2020 | Williams et al. | |
| 2020/0279555 A1* | 9/2020 | Shapiro | G10L 15/22 |

OTHER PUBLICATIONS

"Alexa Voice Service", Amazon.com, Available online at: <https://developer.amazon.com/en-US/alexa/alexa-voice-service>, Retrieved on Feb. 27, 2020, 5 pages.

"Speech-to-Text", Google, Available online at: <https://cloud.google.com/speech-to-text/>, Retrieved on Feb. 27, 2020, pp. 1-7.

"The Comprehensive R Archive Network", R, Available online at: <http://cran.r-project.org>, Retrieved on Feb. 27, 2020, 1 page.

"Transcribing Audio From Streaming Input", Google Cloud, Available online at: <https://cloud.google.com/speech-to-text/docs/streaming-recognize>, Retrieved on Feb. 25, 2020, pp. 1-6.

Final Office Action received for U.S. Appl. No. 16/731,790, mailed on Feb. 15, 2022, 36 pages.

Li, Jinyu et al., "Robust Automatic Speech Recognition: A Bridge to Practical Applications", Published Oct. 12, 2015, Academic Press, an imprint of Elsevier, Waltham, Massachusetts, USA.

N. Niparnan and p. Chongstitvatana, "An improved genetic algorithm for the inference of finite state machine," IEEE International Conference on Systems, Man and Cybernetics, Yasmine Hammamet, Tunisia, 2002, pp. 5 pp. vol.7 (Year. 2002).

Poots et al., "Automatic Annotation of Text with Pictures", IT Professional, vol. 20, No. 1, Jan./Feb. 2018, pp. 36-44.

Pre-Interview First Office Action received for U.S. Appl. No. 16/731,790, mailed on Apr. 15, 2021, 7 pages.

Simmons-Mackie, Nina et al., "Supporting Communication for Adults with Acute and Chronic Aphasia", 2013, Paul H. Brooks Publishing Co., Inc., Baltimore, Maryland, USA.

Yu, Dong et al., "Automatic Speech Recognition: A Deep Learning Approach", 2015, Springer-Verfag London.

Yu, Dong et al., "Automatic Speech Recognition: A Deep Learning Approach", 2015, Springer-Verlag London.

U.S. Appl. No. 16/455,196, filed Jun. 27, 2019.

\* cited by examiner

| | 510 | 520 | 530 | 540 | 550 |
|---|---|---|---|---|---|
| | PERIOD | HASH.CHOICE | HASHCODE.T1 | HASHCODE.T2 | HASHCODE.T3 |
| 501 | 1 | 1 | 1 | 0 | 1 |
| 502 | 2 | 2 | 1 | 1 | 1 |
| | 3 | 3 | 0 | 0 | 1 |
| | 4 | 1 | 0 | 0 | 1 |
| | 5 | 2 | 1 | 0 | 1 |
| 506 | 6 | 3 ~526 | 1 | 0 | 1 ~556 |
| | 7 | 1 | 1 | 1 | 1 |
| | 8 | 2 | 1 | 0 | 0 |
| | 9 | 3 | 0 | 0 | 0 |
| | 10 | 1 | 0 | 0 | 0 |
| | 11 | 2 | 1 | 0 | 1 |
| | 12 | 3 | 1 | 1 | 1 |
| | 13 | 1 | ... | ... | ... |

FIG. 5.

```
###########################################################

#   Finite state machine learning implementation using ASR data in aphasia patients

##################################################### library(doParallel) for Linux implementation
library(shape)
library(diagram)
library(GA)
library(datafsm)

# Load data for reduction-to-practice example, equally balanced among 3 choice states {A,B,C,NULL}, plus a
#    4th NULL state ("no choice").
# period is the epoch in which the choice action materialized. The period and choice columns are integer
#    vectors.
# Predictor columns 3 to 5 represent probability or match-fitness (e.g., from Amazon AWS Lex or Google Cloud
#    Speech API) associated with hash-indexed target words or concepts, which typically manifest polysemy
#    and are associated with 3 alternative pictograms that user points at to choose.

# Transform probability in columns 3 to 5 to integer [0,1] as follows:
# If all three have probability > 0.9, then set all 3 equal to 1.
# If two column values have probability > 0.6, then set the top 2 equal to 1 and the other equal to 0.
# If one column has probability > 0.6 and the others have probability < 0.3, then set top 1 equal to 1 and the
#    other 2 equal to 0.
# If none of the three columns' values has probability > 0.3, then set all 3 column values equal to 0.
# In case of a two-way tie for bottom 2 and both are < 0.6, set both columns equal to 0.

# Create separate FSM models for each match 3-vector, with vector elements sorted from lowest hashcode to
#    highest.
# Inverted index retrieves the FSM model for the matched 3-vector.

cdata <- read.csv(file="c:/0_cerdsm/IP/aphasia/dat.csv", header=TRUE,
          colClasses=rep("integer",5))
head(cdata)
# period  hash.choice  hashcode.t1  hashcode.t2  hashcode.t3
#   1       1            1            0            1
#   2       2            1            1            1
#   3       3            0            0            1
#   4       1            0            0            1
#   5       2            0            0            1
6       3            1            0            1 fsm <- evolve_model(cdata, seed=52, measure=c("accuracy", "sens", "spec", "ppv"),
         cv=TRUE, k=5, popSize=200, pcrossover=0.6, pmutation=0.1, maxiter=50,
         run=25, ntimes=10)
Iter = 48 | Mean = 0.477 | Best = 0.494 summary(fsm)
Genetic Algorithm Settings:
# Population size     = 200
# Number of generations = 5234
# Elitism             = 10
# Crossover probability = 0.6
# Mutation probability  = 0.1
```

FIG. 9A.

CONTINUES IN FIG. 9B

CONTINUES FROM FIG. 9A

```
# Finite State Machine Settings:
# Actions = 3
# States  = 4 including NULL

# Results:

# Iterations For This Run         ≈ 60
# Training Data Fitness Function Value = 0.454

# (Bit String Form) of Solution:
#  x1  x2  x3  x4  x5  x6  x7  x8  x9 x10 x11 x12 x13 x14 x15 x16 x17 x18 x19 x20 x21 x22 x23 x24
#   0   0   1   1   1   1   0   1   0   1   1   1   0   1   0   1   0   0   1   1   0   0   0   0
# x25 x26 x27 x28 x29 x30 x31 x32 x33 x34 x35 x36 x37 x38 x39 x40 x41 x42 x43 x44 x45 x46 x47 x48
#   0   0   0   0   0   1   1   0   0   0   1   0   1   1   1   0   1   1   0   0   1   1
# x49 x50 x51 x52 x53 x54 x55 x56 x57 x58 x59 x60 x61 x62 x63 x64 x65 x66 x67 x68 x69 x70 x71 x72
#   0   0   0   1   0   1   0   0   0   0   0   0   0   0   1   1   0   1   0   0   0   1   1

# State Matrix of Solution:
#      match.t1FALSE:match.t2FALSE:match.t3FALSE
# [1,]                          2
# [2,]                          2
# [3,]                          3
# [4,]                          2
#      match.t1TRUE:match.t2FALSE:match.t3FALSE
# [1,]                          4
# [2,]                          2
# [3,]                          4
# [4,]                          4
#      match.t1FALSE:match.t2TRUE:match.t3FALSE
# [1,]                          4
# [2,]                          4
# [3,]                          4
# [4,]                          2
#      match.t1TRUE:match.t2TRUE:match.t3FALSE
# [1,]                          4
# [2,]                          4
# [3,]                          1
# [4,]                          3
#      match.t1FALSE:match.t2FALSE:match.t3TRUE
# [1,]                          4
# [2,]                          2
# [3,]                          4
# [4,]                          2
#      match.t1TRUE:match.t2FALSE:match.t3TRUE
# [1,]                          4
# [2,]                          3
# [3,]                          2
# [4,]                          4
```

FIG. 9B.

CONTINUES IN FIG. 9C

CONTINUES FROM FIG. 9B

```
#     match.t1FALSE:match.t2TRUE:match.t3TRUE
# [1,]                        4
# [2,]                        4
# [3,]                        4
# [4,]                        3
#     match.t1TRUE:match.t2TRUE:match.t3TRUE
# [1,]                        4
# [2,]                        1
# [3,]                        1
# [4,]                        3

# Action Vector of Solution:
# [1] 1 3 3 2

# Variable Importance in 8 states (3-bit predictor columns):
# match.t1FALSE:match.t2FALSE:match.t3FALSE
#                      44.8   NULL choice
# match.t1TRUE:match.t2FALSE:match.t3FALSE
#                      34.6
# match.t1FALSE:match.t2TRUE:match.t3FALSE
#                      74.1
# match.t1TRUE:match.t2TRUE:match.t3FALSE
#                      90.9
# match.t1FALSE:match.t2FALSE:match.t3TRUE
#                     100.0
# match.t1TRUE:match.t2FALSE:match.t3TRUE
#                       0.0
# match.t1FALSE:match.t2TRUE:match.t3TRUE
#                      63.4
# match.t1TRUE:match.t2TRUE:match.t3TRUE
94.5 vector indicating what action to take for each state
action_vec(fsm)

# graph FSM    bot  lt   top  rt
op <- par(mai=c(1.5, 0.5, 0.5, 1.0))
plot(fsm, action_label=c("A", "B", "C")) # state-transition diagram
plot(estimation_details(fsm))       # fitness of model vs. GA generation
par(op)
```

FIG. 9C

TOOL FOR ASSISTING PEOPLE WITH SPEECH DISORDER

INCORPORATION BY REFERENCE; DISCLAIMER

Each of the following applications are hereby incorporated by reference: application Ser. No. 16/455,196 filed on Jun. 27, 2019; application No. 62/787,095 filed on Dec. 31, 2018; application No. 62/690,943. The Applicant hereby rescinds any disclaimer of claim scope in the parent application(s) or the prosecution history thereof and advises the USPTO that the claims in this application may be broader than any claim in the parent application(s).

BACKGROUND

Language- and communication-impaired persons face many impediments to activities that involve communication with others—both with individuals with whom they are in close physical proximity and other individuals with whom they interact at a distance, as by telephony. Various types of communication disorders exist. For example, aphasia and dysarthria, which each present significant problems for individuals in communicating, at home, in the workplace, in health services, and in social situations. Patients with aphasia often know what they want to say but are unable to find the words to express it. In many instances, they may mean to say one thing but instead say another thing. Dysarthria is a language disorder in which an individual's ability to produce language is compromised by neuromuscular or anatomical abnormalities in the vocal tract or head and neck. Dysarthria is characterized by abnormal or absent articulation of phonemes that comprise words or other meaning-bearing vocal gestures.

Frequent failures to be understood lead to frustration and despair, both for the affected individual and for their caregivers and others in social situations. Moreover, while there have been attempts to provide technological solutions through assistive technologies and decision support systems, these technologies, which typically utilize automatic speech recognition (ASR), have significant drawbacks including being prone to high error rates, which often leads to increased frustration and ultimately discontinued use. These systems and cannot provide the reliability and accuracy of the systems and processes proposed in the present disclosure.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein provide assistive or augmentative means to enhance the fluency and accuracy of persons having speech disabilities. These technologies may automatically ascertain and dynamically improve the accuracy with which automatic speech recognition (ASR) systems recognize utterances of persons having aphasic, apraxic, anomic, dysarthric, or similar speech conditions. At a high level and according to an embodiment, following system initialization or a model training phase, digital information representing a user's utterance is received. The digital information may comprise digitized audio speech samples of an utterance emitted by a human speaker having a speech disorder. The digital information is processed using an ASR system to determine a set of candidate words or phrases matching or corresponding to the speaker's utterance.

From this set of candidate words (or phrases), or from a subset comprising those words having a greater likelihood of matching, one or more corresponding concepts are determined for a particular candidate word (or phrase). In some embodiments, this may be facilitated using a finite state machine (FSM) model, thereby enabling such embodiments to learn or become tailored to particular users. Further, in some embodiments, contextual information may be utilized to further determine the corresponding concepts. Based on the concept(s), a set of pictograms, each corresponding to a concept, is determined. The set of pictograms then may be presented to the speaker so that the speaker may select the pictogram corresponding to the best match of his or her intended meaning associated with the utterance. An action corresponding to speaker's selection then may be performed. For example, in an embodiment the action comprises digitally synthesizing text-to-speech for the concept or corresponding to the pictogram, and playing it via a speaker or other acoustic transducer such that can be heard by the speaker or a human caregiver, either nearby or remotely.

In some embodiments, the speaker's selection may be utilized, along with the alternative concepts corresponding to the other presented pictograms, to update the finite state machine (FSM) model. Further, in some embodiments, information about the speaker's selection and/or alternative concepts corresponding to the other presented pictograms may be used to update an inverted index of the word/concepts and corresponding top candidate matches from the ASR system. These embodiments using the FSM model in conjunction with the ASR system, are more accurately able to predict the speaker's intended meaning when he/she subsequently emits speech that the ASR system determines resembles indexed utterance. Subsequent "repeat" occurrences strongly resembling a given utterance may be more effectively interpreted to identify and retrieve the previously stored concepts and pointers to the associated pictograms from the inverted index. Thus the FSM provides increasing accurate outcomes thereby enabling these embodiments of the system to actually learn a speaker's meaning for a particular word or utterance. In this way, these embodiments can dynamically adapt to the ASR-recognized utterances and subsequent concept-associated pictogram choices of the human user, to assist the user in an emotionally supportive and hope-sustaining manner. In this way, embodiments of these technologies improve upon conventional ASR-based assistive approaches and further mitigate the impact of functional disability on the speaker's caregivers as well as improve quality-of-life for the speaker.

BRIEF DESCRIPTION OF THE DRAWINGS

The present invention is described in detail below with reference to the attached drawing figures, wherein:

FIG. 5 depicts a table depicting rows representing speaker-utterance-selection occurrences with dichotomized confidence values corresponding to three choices of pictogram-represented concepts and the speaker's choice, for use in an embodiment of the disclosure;

FIGS. 9A-9C. illustratively provides an example embodiment of a computer program routine for processing speech to determine an action or concept corresponding to a speaker's intent using a FSM model and ASR system, described in connection to the method of FIG. 2A.

DETAILED DESCRIPTION

Figure 1A:
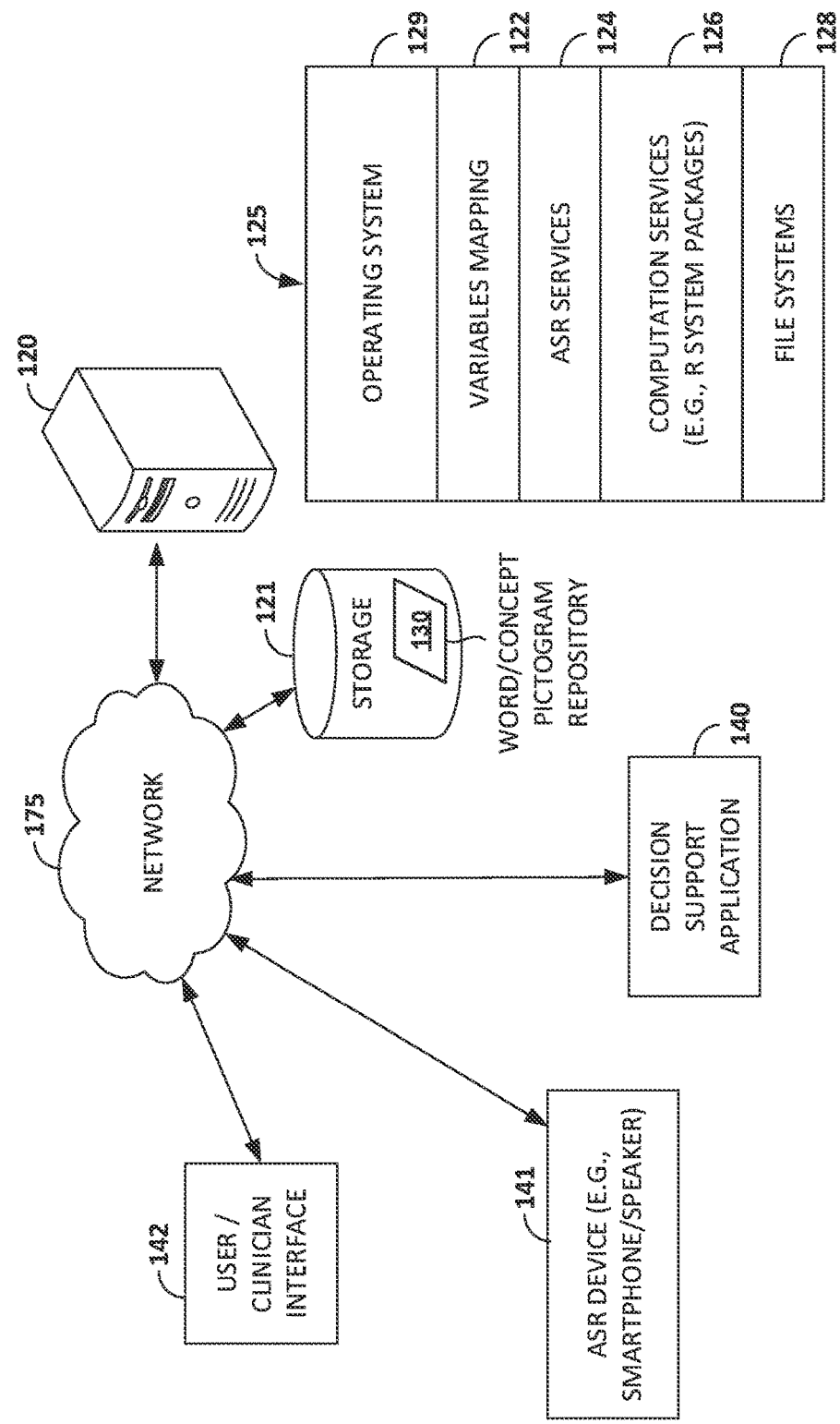
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

At a high level, this disclosure describes, among other things, improved systems and methods for enhancing the fluency and accuracy of a speaker, and in particular, a disabled speaker or speaker in a noisy environment. At a high level and according to an embodiment, digital information representing a user's utterance is received. The digital information may comprise digitized audio speech samples of an utterance emitted by a human speaker having a speech disorder, and may be received from an acoustic sensor, such as a microphone, which may be part of a smart phone or smart speaker, in an embodiment. The samples may represent one or more utterances from the speaker and may be received in near real-time (and/or may be streaming) from one or more acoustic sensors. In some embodiments, the samples may comprise historical or past utterances of the speaker, which may be used for initializing or training the system. In particular, as described herein some embodiments are trained using historical utterances of the user or speaker to develop a machine-learning model, such as a finite state machine (FSM) model and word/concept indicia.

The digital information (e.g., digitized speech samples) is processed using an automatic speech recognition (ASR) system to determine a set of candidate words or phrases (or text strings) corresponding to or matching the speaker's utterance(s). In an embodiment, the ASR system provides a plurality of candidate matched words or phrases with a corresponding likelihood or figure-of-merit metrics, which denote the match quality or probability of each word or phrase representing the speaker's utterance. For example, in an embodiment, the figure-of-merit comprises a numerical confidence or probability with a value between 0 and 1 representing the closeness of matching (inverse of distance) or the likelihood that the ASR-matched word or phrase correctly represents the user's speech utterance.

From this set of candidate words (or phrases), or from a subset comprising those words having a greater likelihood of matching, one or more corresponding concepts are determined for a particular candidate word (or phrase). In an embodiment, an inverted index is utilized; for example, the ASR system may provide a subset of N-matches or candidate words or phrases, which correspond to the most likely words or phrases matching the user's utterance. In an embodiment, N is between three and approximately 10 matches. In an embodiment, a candidate word or phrase is hash-encoded and mapped to one or more related concepts via the index. The word or concept indicia corresponding to the top-N matches (of candidate words or phrases from the ASR system) are determined and retrieved using the inverted index. In some embodiments, this may be facilitated using a finite state machine (FSM) model, as described herein. Thus the likely candidate words and phrases corresponding to the utterances are associated with one or more word or concepts, which in turn are associated with a pictogram as described below. In some instances, these corresponding word(s) or concept(s) determined using the index might be the same as the candidate word(s) or phrases from the ASR system.

By way of example and without limitation, suppose an utterance comprises the sound of whit. Using digitized samples of this sound, the ASR system may provide a set of three candidate words (thus here N=3), such as (a) what; (b) it; and c) wet. FIG. 3B provides an illustration corresponding to this example. With reference to FIG. 3B, item 390 shows the matches returned by the ASR system representing three candidate words. In some embodiments, hashcodes (or hashes) are used to represent the candidate words, as described above, and a hashcode corresponding to each candidate word is returned, such as hashcode 375 corresponding to "what". Additionally, in some embodiments, a corresponding likelihood (e.g., a confidence value or figure-of-merit) of these words matching is also provided (e.g., 0.82, 0.16, and 0.95, for what, it, and wet, respectively). For example, item 395 shows a 0.82 confidence that the utterance matches the word "what". Using an FSM and inverted index, as described here, a set of corresponding concepts is determined, for instance, in this example: the user has a question; the user wants something or is pointing to something, or the user is thirsty.

In some embodiments, contextual information may be utilized to further determine the corresponding concepts. By way of example and without limitation, contextual information may include information such as the time of day, user activity information, which may include user activity patterns or routines or user schedule information. For instance, if a candidate matched word from the ASR system is "wet" and if the current time of day is when a user typically bathes, then the concept of shower or wash may be more likely to be included. But where the time of day is not when the user typically bathes or washes, then the concept of "shower" may be less likely to be included verses other concepts, such as the concept thirsty. Nevertheless, in some embodiments, depending on the figure-of-merit metric or probability of the other alternative concepts, a pictogram corresponding to shower may still be presented to the user.

Based on the concept(s), a set of pictograms, each corresponding to a concept, is determined. The set of pictograms then may be presented to the speaker so that the speaker may select the pictogram corresponding to the best match of his or her intended meaning associated with the utterance. For instance, as shown in the example of FIG. 3B, three pictograms are displayed to the user via a graphical user interface 370: a question mark pictogram 372, a pointing hand pictogram 374, and a glass of water pictogram 376. While it is contemplated that a large number of selections of pictograms may be presented to the user, in an embodiment, two to five pictograms are presented, form which the user may chose. These pictograms may correspond to the most probable matching words from the ASR system (based on the figure-of-merit or confidence values) and/or the most probably transition from the FSM model. In some embodiments, a storage repository containing word/concept pictograms (such as item 130 described in connection to FIG. 1A) for the concept candidates is accessed and pictograms are received for the top-N indicia. In an embodiment, the pictograms are presented via a graphical user interface 370 on a user computing device (or "user device" such as computing device 900 of FIG. 1B) having a user interface that is able to display an image and receive a user selection. (For example and as described in connection to FIG. 1B, computing device 900 includes presentation component(s) 916 for displaying or presenting pictograms and I/O components 920 for receiving the user's selection.) For example, a touchscreen, which may be on a tablet, smartphone, or computer display or a computer monitor/display and an input means, such as buttons, mouse, or joystick for the user to input a selection.

An action corresponding to speaker's selection then may be performed. For example, in an embodiment the action comprises digitally synthesizing text-to-speech for the concept or corresponding to the pictogram, and playing it via a speaker or other acoustic transducer such that can be heard by the speaker or a human caregiver, either nearby or remotely. In some embodiments, the speaker's selection is utilized to update (or to generate in the initial instance or in an training phase) a finite state machine (FSM) model with the most likely alternatives (e.g., the top N alternative concepts or the alternative pictograms presented to the user) and selection made by the speaker. In particular, the FSM model may be generated and updated according to an embodiment of the process described above or in connection to FIG. 2A and FIG. 7, by using historic utterances by the speaker, the speakers resulting selection, as determined from the one or more concepts corresponding to the top matching candidate words provided by the ASR system, and the alternative concepts (or pictograms representing the concepts) that the speaker did not chose. Additional details of the FSM model are described in connection to FIGS. 2A and 7.

Further, in some embodiments, information about the speaker's selection and/or alternative concepts corresponding to the other presented pictograms may be used to update an inverted index of the concepts and corresponding top candidate matches from the ASR system. For example, in an embodiment and as further described herein, hashcodes of the top-N ASR-determined words or text strings are assembled into a hashcode-sorted 3-vector, which is then stored in an inverted index file structure and used for identifying and retrieving the previously stored concepts. In particular, an inverted index also may be created and maintained, which may comprise 3-items or higher-order vectors of alternative words or concept indicia and their corresponding pictograms. In his way, choices made by the user may be catalogued and retrieved so that embodiments of these technologies can provide statistically robust quantitative interpretations and electronic communication thereof.

Embodiments using the FSM model in conjunction with the ASR system are more accurately able to predict the speaker's intended meaning when he/she subsequently emits speech that the ASR system determines resembles indexed utterance. Subsequent "repeat" occurrences strongly resembling a given utterance may be more effectively interpreted to identify and retrieve the previously stored concepts and pointers to the associated pictograms from the inverted index. For example, for a particular user, does the utterance corresponding to wet mean I have to go to the bathroom or I'm thirsty. In some embodiments, an FSM model may be created, based on prior top-N probe concepts, one or more top-N alternatives, and selections made by the user from an M-number of trials, wherein the top-N probe concepts may be hash encoded and stored in an N-vector inverted index. The resulting FSM model may be stored in persistent machine-readable storage and subsequently retrieved and applied when new utterances from said user are received and processed by the ASR system, yielding a new set of top-N matches and their numerical figure-of-merit metrics. In some embodiments, the FSM model may further hashcode and sort the current utterance and its top-N matches to form an N-vector, wherein the N-vector is used to retrieve one or more extant records of the same N-vector, one or more concept-related pictograms associated with the N-vector's components, and the user's previously stored historical selection from among these pictograms.

Moreover, some embodiments using the FSM model can account for contextual information. Thus, it may be determined that for a particular speaker the utterance "whit" most likely refers to the matching word "wet," and that during the mornings, the corresponding concept (as determined using the trained FSM model) is "I have to pee." Thus a graphical user interface may present the user with a pictogram for a toilet in response to receiving the utterance "whit." In some embodiments, the pictogram corresponding to the most likely concept may be presented as the first or left-most selection. Other pictograms presented may correspond to concepts such as "I am thirsty" or "I want to bathe." Continuing with this example, the same utterance "whit" by the same speaker but received at a different time of day (or following another particular utterance or in the presence of another person or based on some other context) might most likely correspond to another concept. For instance, for this particular speaker, from the FSM model and inverted index, it may be determined that the utterance "whit" (which again may be determined by the ASR system to most likely refers to the matching word "wet,") when uttered around 5 pm corresponds to the concept of cocktail or drink. (I.e., the speaker desires a cocktail.) Thus one of the pictograms presented to the user for selection may be a representation of a martini glass.

In some embodiments, a genetic or evolutionally algorithm, such as described in connection to FIG. 2A, may be utilized to determine the FSM model and in particular to determine an optimum "action-vector" representing the accrued set of 'utterance-pictogram' pairs from among the large set of candidate solutions. Still further, in some embodiments, information representing to the speaker's selection also may be stored so that where longitudinal sequences of the speaker selecting particular pictograms occurs, these sequences may be analyzed statistically for determining accuracy of the ASR system's recognition of the user's utterances and for further improving the FSM model for retrieving the likeliest concepts and the corresponding pictograms most likely to be assented-to by the user, based on their historical selection patterns.

As described above, various types of communication impairments exist that limit or introduce impediments to communication for these speakers with others. Patients with aphasia, for example, often know what they want to say but are unable to find the words to express it. In many instances, they may mean to say one thing but instead say another thing. In the case of apraxic aphasic speech, the problem lies with the brain communicating to the muscles of the mouth. Patients have the correct word in mind but are unable to move the muscles of the mouth to speak it. Many, if not most of those afflicted suffer impairments of memory, short-term memory formation, and loss of executive functions. Dementia usually affects some aspect of speech fluency or comprehension or both. Indeed, difficulties with speech are often the earliest detected symptoms in people with dementia.

Dysarthria is a language disorder in which an individual's ability to produce language is compromised by neuromuscular or anatomical abnormalities in the vocal tract or head and neck. Dysarthria is characterized by abnormal or absent articulation of phonemes that comprise words or other meaning-bearing vocal gestures. It is a condition in which problems involve the muscles and larynx and other structures that together accomplish speech production, often making it very difficult to pronounce words in a manner that is intelligible to others. Any of the speech subsystems (respiration, phonation, resonance, prosody, and articulation) may be impaired, interfering with intelligibility or audibility or both. Examples of conditions in which dysarthria occurs include stroke, post-surgical or post-irradiation head-and-neck cancer, brain tumor, traumatic brain injury (TBI), cerebral palsy, Guillain-Barré syndrome, amyotrophic lateral sclerosis (ALS), Niemann-Pick disease, and Wilson's disease.

By contrast to dysarthria, some communication or language disorders primarily involve cognitive and/or memory processes. Aphasia, for example, is an acquired neurogenic language disorder in which an individual's ability to produce or comprehend language is compromised. It can be caused by a number of different underlying pathologies but generally involves physical damage to the individual's brain, such as atrophy and neurofibrillary tangles in the brain in Alzheimer's disease, tissue damage following ischemic or hemorrhagic stroke, lesions caused by a traumatic brain injury or infection, and the like. Aphasia can also be associated with certain neurodegenerative diseases, as is the case in Primary Progressive Aphasia (PPA). According to the National Institute of Neurological Disorders and Stroke, approximately 1 million people in the United States suffer from aphasia, and aphasia is a common consequence of strokes (prevalence estimates for aphasia among stroke patients vary, but are approximately thirty percent.

Anomia, which is the inability to access and retrieve words or name items or concepts, is a common manifestation of aphasia in dementia. Anomia can take several different forms, but for the purposes of this disclosure we mostly want to consider anomia characterized by circumlocution and paraphasias, which are unintended errors in word production. There are several categories of circumlocutionary and paraphasic errors. Semantic errors arise when an individual unintentionally produces a word that is semantically-related to their original, intended word (their "target word"). An example of such a semantic error would be saying "dog" when one intended to say "cat." Phonemic errors are when the speaker produces an unrelated word that is phonemically related to their target (saying "hat" instead of "cat", for example. It is also possible for a production error to be of 'mixed' type (that is, both semantically and phonemically related to the target word; for example, saying "rat" instead of "cat"). Individuals with anomia also produce unrelated errors, which are words that are, at most, tenuously or idiomatically semantically or phonemically related to their intended target word: for example, producing "whiz" instead of "zipper" in connection with dressing or urinating. Each of these categories shares in common that the word produced by the individual is a "real" word that can be recognized by an ASR system in embodiments of the technologies described herein.

There is another family of anomic errors, called neologisms, in which the individual produces non-word productions, or, in more severely impaired individuals, groans or grunts that (to a human listener or to the ASR system) have some similarity to the intended word. The individual may produce 'abstruse' neologisms, in which the produced phonemes bear no discernable similarity to the intended lexical item in the index language (for example, an English-speaker saying "cuchara" for "spoon"). Despite the abstruseness, the individual replicates the same neologism consistently and often emphatically, with the same intended meaning, in much the same manner as small children may do early in language-acquisition.

Further compounding these problems, words and their usage are influenced by the speaker's culture. Therefore, it can be important to take cultural and linguistic context into account in order to understand a speaker's intent, which is often beyond the ability of many listeners and beyond the capabilities of the ASR software used by conventional assistive technologies. This is particularly so where a speaker's language skills, understanding, and executive function decline, as in the dementias. According to one study by Samuelsson, language impairment "includes word-finding problems, syntactic problems, and finally also a disturbance of pragmatic functions. The linguistic problems are related to cognitive impairments in especially the episodic and semantic memory systems together with declining executive functions" [Samuelsson C, Hydén L. Intonational patterns of nonverbal vocalizations in people with dementia. Am J Alzheimer's Dis & Other Dement 2011; 26:563-72]. In later stages of dementia, for example, the patient may only have a small set of repetitive words that gradually regress into nonverbal vocalizations, such as word-fragments or grunts and groans. Comprehension of speech acts having non-literal meanings may be needed to understand the speaker's intended meaning. This may require an understanding of both the words uttered and the implicit meanings behind the words, which in turn is culture-bound. Each culture has its own way of using language, with differences in how desires, annoyance, pain, and so forth, are expressed, both verbally and pictorially.

Paradoxically, for a person with aphasia retrieving the desired word or concept frequently proceeds by circumlocution, in which the person emits a series of utterances that all have peripheral or tangential relevance to the person's intended meaning but do not directly include the correct word or concept. The "prime" word or concept activates the "semantic field" in the person's mind corresponding to the "probe" word or concept and paradoxically slows the naming of semantically related probes. Likely this is because the correct choice becomes embedded in a field of semantically related lexical items having similar activity levels or valence. Impaired selection among word forms that are connected to the same semantic field can be caused by degradation of a semantic field, changes in the connections of the semantic field with word form networks, or changes within the word form networks themselves. The net result is that the correct word and words that are closest to the meaning intended by the speaker tend to take the longest time to recall, or are not retrieved at all. Words that are remote from the meaning that is intended tend to come to the person's mind quickly and in large quantities, which compounds the frustration that the affected person experiences. Frustration is exacerbated on account of the undesired flood of incorrect words and concepts, which deters or distracts the person in her/his further pursuit of the word they wish to express.

It is also possible to have dysarthria and aphasia concomitantly. This situation commonly occurs in Parkinson's disease, one of the relatively common chronic conditions toward which the present invention is directed. The reported standardized incidence rates of Parkinson's disease (PD) are 8 to 18 per 100,000 person-years. The average age of diagnosis for PD is 60 years, but the disease frequently develops in individuals of working age. Normal respiration, phonation, and articulation are fundamental for producing well-coordinated speech, while a breakdown in any of these subsystems, or in their coordination, can lead to disordered speech. Parkinson's disease and its common signs (tremor, muscular rigidity, bradykinesia, akinesia, etc.) affect the subsystems of respiration, phonation, and articulation that govern speech motor control. Disordered oral communication affects most PD patients: soft voice, monotone, breathiness, hoarse voice quality and imprecise articulation are common symptoms. Voice problems are typically the first to occur, while other disorders, such as prosody, articulation changes, diminished fluency, and anomia appear later.

Amyotrophic Lateral Sclerosis (ALS), a less-common chronic condition to which the present invention is directed, also tends to have concomitant dysarthria and aphasia as the disease progresses. Between eighty and ninety-five percent of patients with ALS eventually develop speech impairments, such as defective articulation, slow laborious speech, and hypernasality. Because of the long course of ALS, often progressing over several decades, the effect of the communication impairment on the patient and caregivers is often severe. People with other motor neuron diseases also tend to develop dysarthric and/or apraxic speech.

To date, communication impediments due to aphasic, dysarthric, or other speech-impairment conditions have not been ameliorated significantly by modern speech-to-text or ASR-based assistive technologies. In particular, the conventional assistive technologies using ASR are prone to high error rates, and are thus often unable to provide assistance, which leads to increased frustration and ultimately discontinued use. For example, both dysarthria and aphasia have proved difficult to computerize with ASR technology, as understanding aphasic speech typically depends on subtle and complex linguistic judgments about the phonological and semantic similarity of words, and requires the listener to interpret phonologically disordered speech.

However, embodiments of the present disclosure provide an improvement to ASR-based technology that successfully assists or augments the communication fluency and accuracy of a person having a language or oral communication impairment. In some ways, embodiments described herein utilize an approach that may be considered to model and handle different patterns of speech, especially impaired speech that arises in seeking assistance with activities of daily living (ADLs) or speech in noisy environments. These technologies thus provide assistive and augmentative means to enhance the fluency and accuracy of speaker communication and mitigate the impact of functional disability on the speaker's caregivers as well as improve quality-of-life for the speaker. Aphasia and dysarthria in stroke patients often resolve within 12 months of the stroke event. As such, the extent for assistive technologies for individuals with aphasia in stroke patients may primarily be in the acute and subacute periods. In other conditions, such as spinal cord injury and cerebral palsy, the dysarthria may be a permanent or lifelong disability, and the potential cumulative benefit of accurate assistive and augmentative support is much greater.

Other problems with the conventional assistive technologies include: (1) poor handling of dysarthric speech, even with speaker training of a speaker-dependent ASR system, yielding high error rates which lead to discontinued use; (2) inadequate handling of aphasic speech, including circumlocutory speech acts; (3) no functionality for utilizing longitudinal patterns in speech-impaired speakers, such as recency-of-mention or frequency-of-mention of a given word or concept in the course of daily activities; (4) no syntactic or semantic model to handle polysemy of words; (5) no support for context-aware determination of the likeliest "prime" word or concept by performing statistical inference from recent semantic context or speaker choices; (6) static, large collections of pictograms in physical media (such as picture-books or decks of picture-cards) that are difficult for disabled persons to manipulate; and (7) static arrangements of pictograms that are context-agnostic and that compel the user to navigate sequentially through the collection in a manner that is time-consuming, tedious, and interferes with fluency of expression.

Additionally, ASR-based systems have not to date, been utilized to retrieve relevant pictograms for communication-impaired patients to select from. The graphical design of such pictograms that are relevant to the needs of patients will differ according to the condition and its severity—for example, mild cognitive impairment, frontotemporal lobar degeneration, primary progressive aphasia, or Alzheimer's disease. In particular, a novel aspect of some embodiments of the technologies disclosed herein includes functionality for dynamically adapting to ASR-detected utterances and subsequent concept-associated pictogram choices of the human user, to assist the user in an emotionally supportive and hope-sustaining manner. Conventionally, assistive human caregivers of aphasic or dysarthric persons are advised to resist the urge to finish the speaker's sentences or offer words for the speaker to assent or dismiss. This advice is predicated on the rationale that it is desirable to rush or coerce the speaker, which could make the speaker feel that his/her disability is more hopeless or intractable than it is or, alternatively, make the speaker feel that their caregiver's patience is being taxed, inducing anxiety in the speaker about the caregiver's abandoning the language-understanding effort. However, when an automated system, such as the embodiments described herein, seemingly spontaneously offers a range of choices and the speaker's selection from among the offered choices (or not) is entirely under the speaker's own control, there is no diminution of the speaker's hopefulness for improvement in their condition nor is there any sense of coercion, impatience, or rushing. Frustration and anxiety are reduced compared to conventional approaches and the prior art.

Hidden Markov Models (HMM) technology may be utilized for ASR systems. However, in some embodiments, the speech recognition operation may utilize deep learning techniques such as long short-term memory (LSTM), recurrent neural networks (RNNs), convolutional neural networks (CNNs), and restricted Boltzmann machines. LSTM RNNs avoid the so-called "vanishing gradient problem" and can learn tasks that require memories of events that happened thousands of timesteps in the past, which is important for speech. The raw output from an ASR system may comprise a stream of words. With some effort, this can be transformed into a format which is more readable by both humans and machines. Although conventional algorithms exist for the segmentation of the raw text stream into sentences. These algorithms present problems when applied to impaired speech. First, utterance boundaries are important when analyzing the syntactic complexity of speech, which can be a strong indicator of potential impairment. Many measures of syntactic complexity are based on properties of the syntactic parse tree (for example, Yngve depth, tree height), which first require the demarcation of individual sentences. Even very basic measures of syntactic complexity, such as the mean length of sentence, require this information. Secondly, there are many reasons why conventional ASR-based algorithms might not perform well on impaired speech, since assumptions about normal speech do not hold true in impaired speech. For example, in normal speech, pausing is often used to indicate a boundary between syntactic units, whereas in some types of dementia or aphasia a pause may indicate word-finding difficulty instead. Other indicators of sentence boundaries, such as prosody, filled pauses, and discourse markers, can also be affected by cognitive impairments.

In contrast, specific technique(s) and technology utilized by the embodiments of the assistive tool described herein avoids such limitations and thus improve upon conventional ASR-based assistive approaches. Consequently, the impact of functional disability on the speaker's caregivers is mitigated and the quality-of-life for the speaker is improved.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including monitoring and processing user speech, determining, and/or predicting user intent (e.g., a concept) corresponding to an utterance emitted by the user, and presenting a pictogram corresponding to the concept, receiving a selection by the user, and performing an action in response to the selection.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., computing device, such as computing device 900 described in connection to FIG. 1B) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FP- GAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components. In some embodiments, components of environment 100 that are shown as distinct components may be embodied as part of or within other components of environment 100. For example, decision support application 140 may comprise an app running on ASR device 141, such as a smartphone, in an embodiment.

In some embodiments of the technologies described herein, aspects of an assistive tool for users having a speech impairment may utilize data about a population of patients derived from patient electronic health records or other records information. In particular, certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, environment 100 includes network 175, which is communicatively coupled to computer system 120. Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

In some embodiments, operating environment 100 may include one or more electronic health record (EHR) system(s) (not shown) or data stores of health-related records, which may be stored on storage 121, and may further include one or more computers or servers that facilitate the storing and retrieval of the health records. In some embodiments, EHR system(s) and/or other records systems may be implemented as a cloud-based platform or may be distributed across multiple physical locations. The EHR system(s) may further include record systems, which store real-time or near real-time patient (or user) information, such as wearable acoustic sensor or monitor, bedside, laboratory, or in-home patient monitors or sensors, for example, such as ASR device 141.

Example operating environment 100 further includes a user/clinician interface 142 and decision support application 140, each communicatively coupled through network 175. Although environment 100 depicts an indirect communicative coupling between components of operating environment 100, it is contemplated that in some embodiments, components may be communicatively coupled directly. For example, in one embodiment a decision support application 140 operating at least in part on a client device (such as a user-operated computer device like a tablet) includes an interface 142 (which may comprise a graphical user interface), which may be used for accessing patient information from storage 121.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a user-speaker or caregiver for communicating the intent of the speaker based on utterances emitted by the speaker. In some embodiments, application 140 includes or is incorporated into a computerized decision support tool, as described herein. Further, some embodiments of application 140 utilize user/clinician interface 142.

In one embodiment, decision support application 140 comprises an app that runs on an ASR-device 141 such as a user-speaker's smartphone or tablet computer. The application 140, which may operate in conjunction with interface 142, facilitates receiving user utterances, which may be received from an acoustic sensor coupled to ASR-device 141, processing the utterances (or commutating digital information representing the utterances to computer system 120), identifying or displaying (e.g., via interface 142) a set of pictograms representing concepts determined to likely correspond to the speakers intent when emitting the utterances, receiving a selection by the user (e.g., via interface 142) of a particular pictogram, and performing an action corresponding to the selection, such as performing a text-to-speech synthesis of word(s) indicating the concept represented by the pictogram and playing the audio of the synthesized speech (e.g. via interface 142).

In some embodiments, application 140 and/or interface 142 may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-support application 140 may also be used for providing diagnostic services or evaluation of the performance of various embodiments.

In some embodiments, user/clinician interface 142 may be used with application 140, such as described above. One embodiment of interface 142 takes the form of a graphical user interface (GUI) for an application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 operates in conjunction with a Web-based application (which may take the form of an applet or app) or set of applications usable to manage user services provided by an embodiment of the technologies described herein. In some embodiments, interface 142 may comprise one or more interfaces, such as a GUI, which may be utilized to display pictograms to a user or word(s) corresponding to a user's selection or a pictogram, a touch-responsive interface, keyboard, joystick, mouse or other interface operable to receive a user selection and/or input by a user, an acoustic speaker, which may be utilized to play synthesized speech based on a user's selection of a pictogram-concept, and/or an acoustic sensor, which may be used to receive audio information representing the utterances of the user. An example of an interface 142 for presenting pictograms to a user is shown at item 335 of FIG. 3A and item 370 of FIG. 3B.

In some embodiments, interface 142 may facilitate providing feedback, recommendations, providing instructions, reminders, confirmations or notifications (such as confirmation that utterance-related information has been detected or notifications that an utterance was not adequately sensed or that there may be an error, or outputs of other actions described herein, as well as logging and/or receiving other feedback from the user/caregiver, in some embodiments. Interface 142 also may be used for facilitating diagnostic services or evaluation of the performance of various embodiments.

Example operating environment 100 includes ASR device 141 communicatively coupled through network 175 to computer system 120. ASR device 141 is generally responsible for processing digitized acoustic information of a speaker's utterance(s) and outputting (returning) one or more candidate words that match (or likely match) the spoken utterance. In some embodiments, ASR device 141 determines and provides a hashcode-representation of the word or words, and may further provide corresponding confidence values that the word or hashcode matches the utterance. In an embodiment, the confidence value comprises a figure-of-merit that represents a numerical confidence or probability with a value between 0 and 1 representing the closeness of matching (inverse of distance) or the likelihood that the ASR-matched word or phrase correctly represents the user's speech utterance. In some embodiments, ASR device 141 processes digitized utterances of a speaker and outputs or returns a set of hashcodes and corresponding figure-of-merit values or confidence values, which may be ranked based on likelihood or closeness of matching. For example, in an embodiment, the top 3 closest matches are returned by ASR device 141.

Accordingly, ASR device 141 may comprise one or more acoustic sensor components operable to acquire acoustic speech information from a user-speaker, digitize the acoustic information, and determine a set of candidate words most nearly matching the digitized utterance(s). In one embodiment, the ASR system merely receives the acoustic information or already digitized information. For example, in some embodiments, digital information representing past or historical utterances by a speaker may be processed by the ASR device 141 to return a set of candidate words (which may be represented as hashcodes) corresponding to each utterance. In some embodiments, ASR device 141 comprises an ASR system, which may comprise or utilize a backend server or could-based service(s) for performing speech recognition.

Some embodiments of the technologies described herein operate in conjunction with or on top of an ASR system, using an application programming interface. For example, in an embodiment, ASR device 141 comprises or utilizes the Google Cloud Speech-to-Text API ASR system (developed by Google and available at https://cloud.google.com/speech/docs/streaming-recognize, and https://cloud.google.com/speech-to-text/). In another embodiment, ASR device 141 comprises or utilizes Amazon's Alexa Voice Service ASR system (developed by Amazon https://developer.amazon.com/alexa-voice-service). Thus for example, in an embodiment, ASR device 141 comprises an Amazon Echo® smart-speaker device or Amazon Echo Show smart speaker with display monitor. Similarly an embodiment of ASR 141 may comprise a smartphone or tablet running an ASR service, such as the Alexa app, Google Now, or a voice-recognition service or application.

Some embodiments of ASR device 141 monitor an environment for utterances and process and provide output as utterances are detected. Thus in some embodiments, ASR device 141 operates as a streaming component or service. Some embodiments of ASR device 141 may further comprise an interface component, and/or processing/communications component (not shown). Embodiments of ASR device 141 may store user-derived data locally or communicate data over network 175 to be stored remotely. Some embodiments of ASR device 141 include a monitor interface, which may be embodied as I/O such as buttons and sounds emitted from the ASR device 141, its firmware or software application or app operating on a user's mobile device or computer system 120, and in an embodiment may facilitate communicating information from ASR device 141 to computer system 120. Additionally, some embodiments of measurement device 141 include functionality for processing utterance information locally, communicating the information to computer system 120 or backend server for example, where it is processed. In some embodiments the processing functionality, performed on ASR device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to storage 121 and other components of environment 100.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140, ASR device 141, or interface 142 may operate on or utilize computer system 120. Similarly, a portion of computing system 120 may be embodied on user interface 142, application 140, or ASR device 141. In one embodiment, system 120 comprises one or more computing devices, such as a server, desktop computer, laptop, or tablet, cloud-computing device or distributed computing architecture, a portable computing device such as a laptop, tablet, ultra-mobile P.C. smart-speaker, or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of supporting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, variables mapping service (or model variables indexing service) 122 facilitates identifying, accessing, retrieving, and/or indexing for storage concepts to candidate words matching a speaker's utterance(s). For example, as further described herein, some embodiments utilize an FSM model and inverted index file structure, which may index hashcode information representing top ASR matches of a speaker utterance and may be utilized with the FSM model for identifying concepts corresponding to the hash encoded utterance information. In some embodiments, variables mapping service 122 may also facilitate retrieving FSM-model variables, which may include frequent item sets, extracting database records, and/or cleaning the values of variables in records. Embodiments of records/documents ETL service 124 perform extract, transform, and loading for database usage and data storage, which may include one or more FSM models or data used by the models, indices, tables, or other file structures.

Computation services 126 may perform statistical and/or computational software operations, and may include statistical or computational software packages such as, in one embodiment, the R system (the R-project for Statistical Computing, which supports R-packages or modules tailored for specific statistical or computational operations, and which is accessible through the Comprehensive R Archive Network (CRAN) at http://cran.r-project.org) or similar services. In an embodiment, computation services 126 and/or other services of stack 125 may be embodied as one or more software agents or computer programs such as the example embodiments of computer program routine illustratively provided in FIGS. 9A-9C. In one embodiment, computation services 126 comprises the R-System GA (genetic Algorithms) package for implementing genetic (or evolutionary) algorithms, and the R-system datafsm package, which may be used to determine an FSM model. For example, where a number of permutations may exist, such as for an utterance associated with a particular concept, a GA algorithm of computation services 126 may compute a number of mutations of the utterance (e.g., utterances pertaining to the concept "drinking"). Computation services 126 may further look at the goodness of fit for the mutations, which may represent statistically how frequently the mutation matching the concept occurs for use in assembling an FSM model. Computation services 126 also may include natural language processing services (not shown) such as Discern nCode™ developed by Cerner Corporation, ASR processing services, or similar services. In an embodiment, computation services 126 include the services or routines, which may be embodied as one or more software agents or computer software routines such as the example embodiments of computer program routines illustratively provided in FIGS. 9A-9C. Computation services 126 also may include other services or routines for utilizing one or more models such as described in connection to FIG. 2A and the example computer program routines illustratively provided in FIGS. 9A-9c.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in stores information for embodiments described herein. By way or example and without limitation, this information may include digitized information representing user utterances, database(s), indices, model(s), variables for the model(s), pictograms, user-credentials (or data used for identifying or verifying a speaker, so that the correct machine-learning model may be retrieved and used upon receiving utterance-information from the user), recommendations; recommendation knowledge base; recommendation rules; an operational data store, which stores events, frequent itemsets (such as "X often happens with Y", for example), and item sets index information; association rulebases; agent libraries, solvers and solver libraries, and other similar information including data and computer-usable instructions; logic, patient- or user-derived data; care-provider information, or other data, for example. It is contemplated that the term data includes any information that can be stored in a computer-storage device or system, such as user-derived data, computer usable instructions, software applications, or other information. In some embodiments, data store 121 comprises the data store (s) associated with ASR device 141. Further, although depicted as a single storage data store, data store 121 may comprise one or more data stores, or may be in the cloud.

As shown in example operating environment 100, storage 121 includes word/concept pictogram repository 130. Embodiments of repository 130 store pictograms or images representing concepts determined to correspond to the user's utterances.

In an embodiment, these pictograms or images are simplified and/or representative of a concept, for instance, the image may be bitonal (e.g., black and white) and may exclude extraneous information that might introduce confusion about what the image represents. Examples of such pictograms or images are often used on public signs or equipment (e.g., men's/women's restrooms, traffic symbols, instructions on equipment such as power-off/on, play, stop, fast-forward, etc.). Some examples of pictograms are depicted within interface 335 on FIG. 3A and items 372, 374, and 376 on FIG. 3B.

Some embodiments of operating environment 100 may also include an assistive communication system interface (not shown). For example, it is contemplated that some embodiments herein may operate in conjunction with or may be part of an assistive communication system.

Figure 1B:
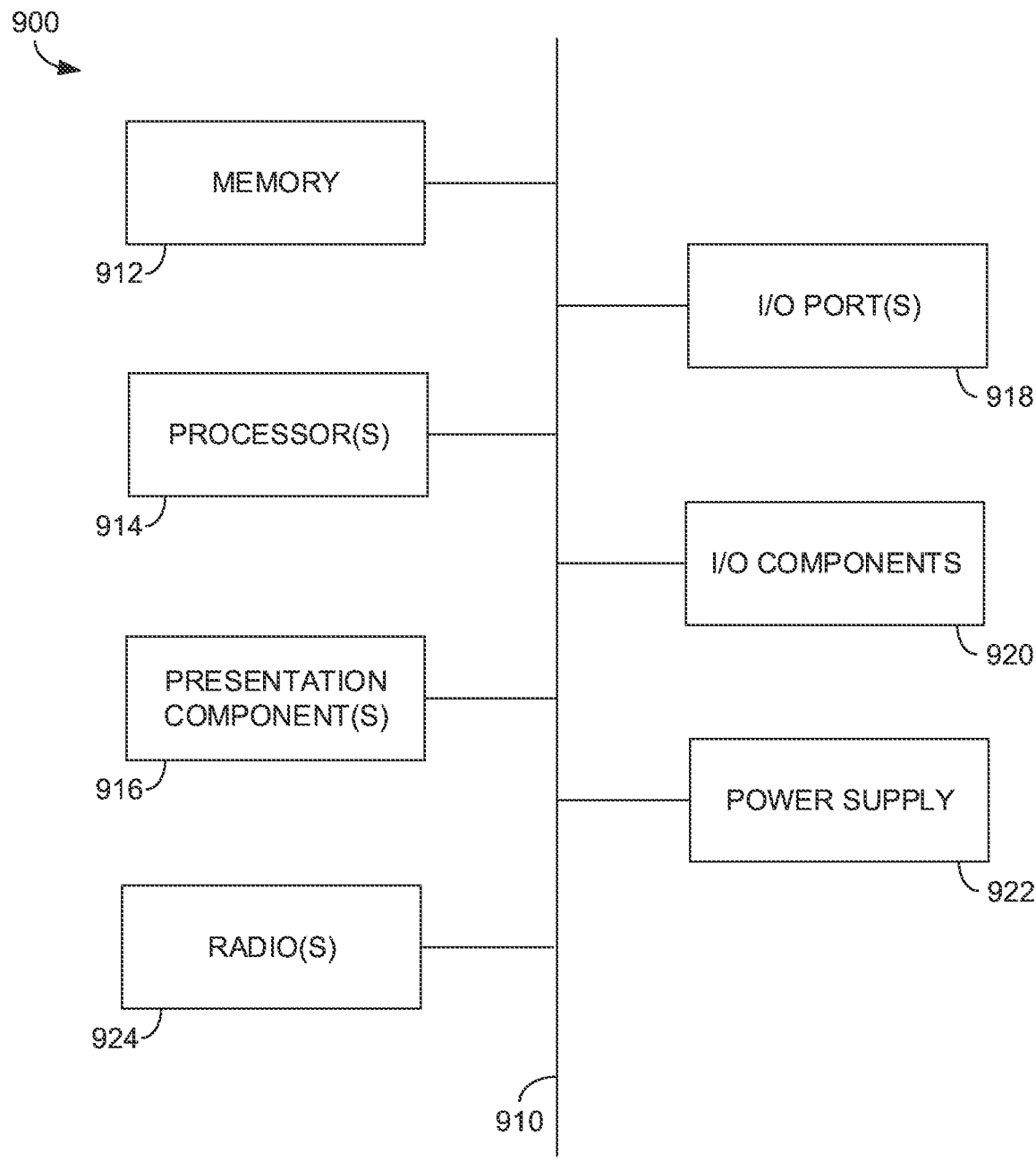

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2A:
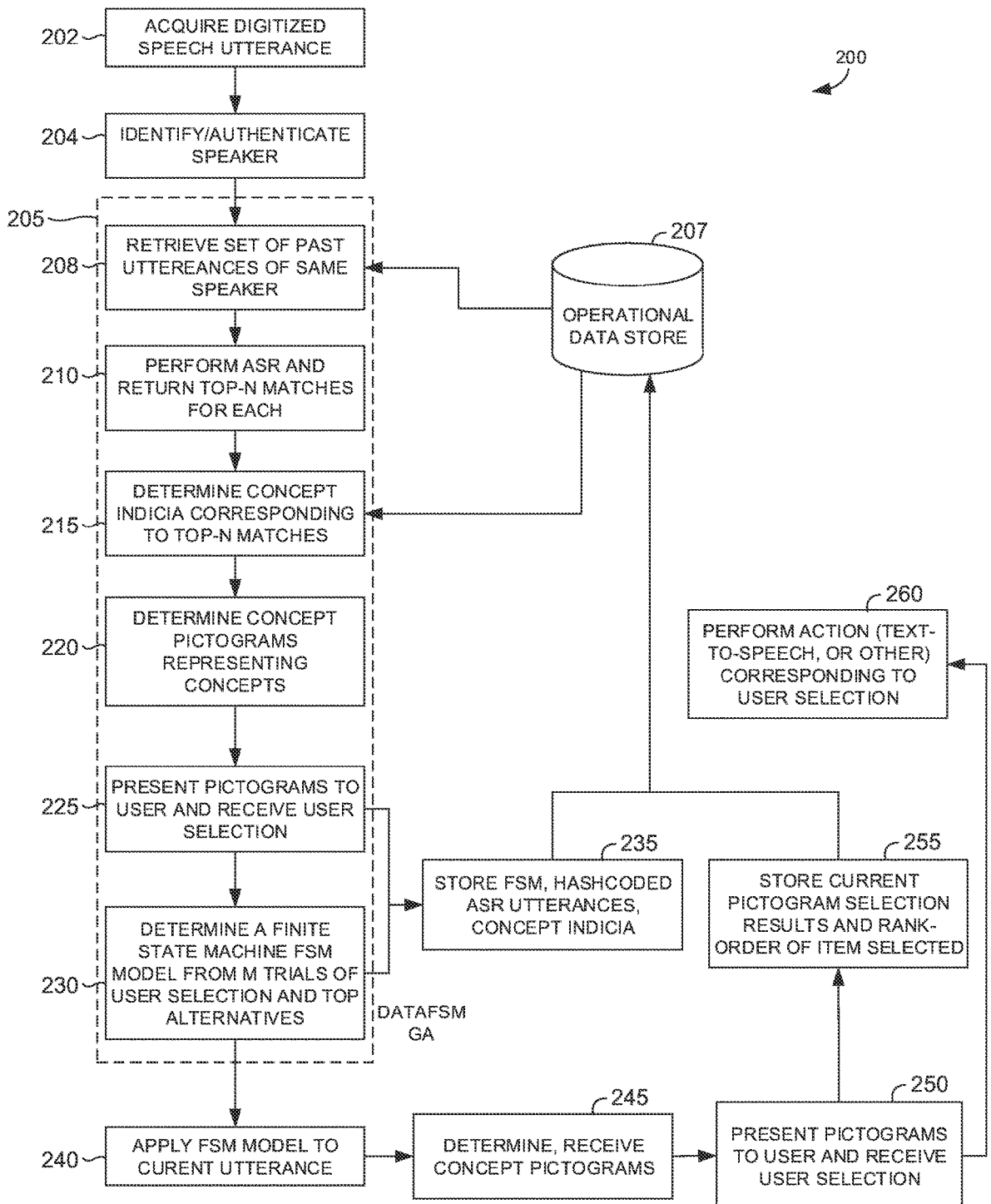
FIGS. 2A and 2B depict a flow diagrams of a computerized method for processing speech to determine an action or concept corresponding to a speaker's intent, in accordance with an embodiment of the disclosure.
Figure 2B:
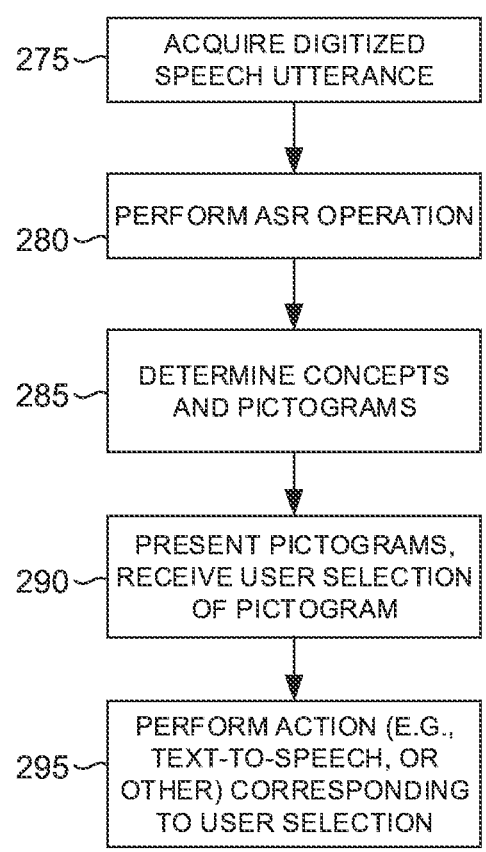

Turning now to FIGS. 2A and 2B, example embodiments are provided of methods for processing speech to determine an action or concept corresponding to a speaker's intent, and are generally referred to as method 200 and method 201, respectively. In some embodiments, aspects of methods 200 or 201 may be carried out using the computer program routine depicted in FIGS. 9A-9C, and may be performed by one or more components of example operating environment 100 (FIG. 1A) and/or computing device 900 (FIG. 1B). With reference to FIG. 2A and method 200 and at a high level, one embodiment comprises: processing digitized streaming speech, analyzing an ASR output of the digitized speech, rendering pictograms corresponding to a plurality of matching words or concept indicia, determined from the ASR output, to the user on a computing device, acquiring the user's choice (if any) of pictogram corresponding to each utterance, determining an FSM model from a series of utterance inputs and pictogram choices so as to rank-order a plurality of alternative concepts (or pictograms representing concepts) according to the likelihood of their representing the speaker's intended meaning, and adaptively refining the accuracy of the FSM model by ongoing updates to the FSM model as additional utterances and choices accrue.

In some embodiments, an index, such as an inverted index, is utilized to identify and return concepts that might represent the speaker's intent, from the set of candidate words or phrases provided by an ASR operation. For example, in an embodiment, a SQL database may be utilized. Further and as described below, the ASR-outputted words or phrases may be hash-encoded and mapped to one or more related concepts. (For example, some embodiments utilize a vector of hashcodes representing the top N candidate matches of the ASR operation from an utterance, which is stored using an inverted file structure.) A concept may be represented by a pictogram, which may be presented to the speaker for possible selection. For instance, in an embodiment the top three or four pictograms may be presented to the speaker for possible selection. These pictograms represent the top concepts, each of which may be mapped or indexed to a top candidate word or phrase returned from the ASR operation. For example, in an embodiment, for a particular concept indicia, a pointer may point to a corresponding pictogram in memory (e.g., in a word/concept pictogram repository, such as item 130 of operating environment 100 (FIG. 1A)) representing the concept.

Initially, in some embodiments, an index may be created of concepts and corresponding phrases or words representing the output of the ASR. The index may be initialized with default mappings and indicia may be provided; for instance, the indicia may be determined using data from a population of users or determined based on an average or typical words and corresponding concepts. In other embodiments, the index may be created and initialized based on historical utterances of the user or by a training process.

In some embodiments, method 200 includes an initialization or training phase (identified as box 205) for creating a machine-learning (ML) model, which may be used for identifying one or more likely concepts corresponding to a word or phrase returned from the ASR operation. For example, as described below, in an embodiment an FSM model is utilized, which may be implemented structurally as a transition matrix. In some embodiments, the ML model may be trained using information from sessions or trials (sometimes referred to herein as cycles) of ASR utterance recognition-pictograms presentation-subsequent user selection of a pictogram. Further, in some embodiments, information about the alternative selections (i.e., concepts or pictograms that were presented but not selected) for each cycle is also captured and used for training the model. For example, in an embodiment, an FSM model is initialized using information (e.g., from the top-N concepts or pictograms presented to the user and user's selection) from between two hundred and approximately twenty thousand trials. In an embodiment reduced to practice, information derived from fifteen-thousand utterances and pictogram selections was utilized for the construction of an FSM model.

Once initialized or trained, the ML model may be applied to current utterances. In an embodiment, based on the user-speaker's utterance and ASR outputted candidate words or phrases, the ML model (e.g., an FSM model) generates or provides a probability-rank-ordered (or confidence-rank-ordered) list of concepts corresponding to a candidate word or phrase. (In some embodiments, the ML model is utilized along with an index structure (such as described above) for identifying and retrieving the concepts.) For embodiments using an FSM model, the list is based on the state of the FSM model (e.g., the immediate prior state of the model). A number of pictograms, each representing a concept in the list, then may be presented to the user, in an embodiment. The speaker's selection of a pictogram (which represents a concept) may be stored along with information about the utterance so that the ML model may be updated. In this way, contextual information (i.e., context, as described above) is able to be utilized for determining a user-speaker's intent based on his or her utterance. Additionally, these embodiments are able to learn the user-speaker's intent or desire (as reflected by the selected concept) corresponding to specific utterances, which to a caregiver may not resemble any intelligible words or seem to correspond to the user-speaker's intent. Moreover, these embodiments are able to discover and utilize semantic or syntactic relationships among a sequence or set of utterances. For instance at a particular time, does "wet" indicate the user wants something to drink, needs to go to the toilet, or is observing something (e.g., it's raining outside). These embodiments may thus reduce the problem of polysemy. Additionally, embodiments using the ML model enable longitudinal sequences of the user's selecting particular pictograms to be analyzed statistically for determining the accuracy of the ASR system's recognition of the user's utterances and for purposes of ongoing improvement of the model for retrieving the likeliest concepts and the corresponding pictograms most likely to be assented-to by the user, based on their historical selection patterns.

Further still, according to some embodiments, the FSM model is produced using a genetic or evolutionary algorithm, which introduces potential mutations into the model. Conceptually, a string of several utterances may be mutated or changed thousands (or millions) of times, and then the set of mutations may be analyzed to identify those that match utterances by the user. For instance, goodness of fit may be used to see how frequently the mutations match. In an embodiment, the genetic or evolutionary algorithm outputs one or more FSM models that include information on the mutations. Information from subsequent user utterances and selections also may be logged and used for updating the FSM model, the next time the genetic or evolutionary algorithm operates. These embodiments are thus capable of adapting to or learning new words or utterances, which can be learned and mapped to corresponding user intent. Thus, even where an ASR-provided output is completely inaccurate, these embodiments are able to learn and provide a pictogram representing a concept more likely to reflect the user's intent. Aspects of an example embodiment actually reduced to practice, which uses a genetic algorithm to generate FSM model, is provided in the computer program routine of FIGS. 9A-9C.

Accordingly and in light of the foregoing, method 200 begins at step 202, wherein a user or speaker's speech utterance is acquired and digitized. Embodiments of step 202 may be performed using an acoustic sensor and an A/D converter, which may be part of an ASR device 141 (FIG. 1A) or computing device 900 (FIG. 1B), such as a smart phone, tablet, or smart speaker. In subsequent steps, the utterance received at step 202 may be referred to as a current utterance. At step 204, the speaker may be identified and/or authenticated (e.g., by recognizing the speaker's voice, image, or from receiving other credentials information from the speaker, such as a biometric, login, or similar information). In some embodiments, method 200 may not authenticate the speaker, but it may be helpful to identify the speaker so that data specific to the speaker may be identified and used to more accurately understand the speaker, such as machine-learned models, indices, or past selections or utterances. In an embodiment, method 204 comprises binding the current entity of interest, to form a data frame (attributes and current date).

As shown in FIG. 2A, method 200 includes box 205, which includes steps 208 through 240. These steps associated with box 205 may be performed as an initialization or training phase for creating an FSM model (or other ML model) as described herein. The FSM model then may be used in step 240 through 250 for identifying one or more likely concepts corresponding to a word or phrase returned from an ASR operation and presenting a set of pictograms to the user-speaker representing the concepts.

At step 208, past utterances of the speaker are received. In some embodiments, step 208 may be performed to facilitate generating a model to more accurately determine a speaker's intent based on the speaker's utterance. Past utterances may be identified based on the speaker's identity. The past utterances may be stored in storage, such as operational data store 207, which may be embodied as data store 121 (FIG. 1A) and may be encoded or stored as digitized audio information.

At step 210, perform automatic speech recognition (ASR) on the utterances of the speaker, and return (i.e., provide or output) the top-N candidate matches for each utterance. Embodiments of step 210 perform an ASR operation on current and/or historic utterances of the speaker. In an embodiment, step 210 may be performed using an ASR device or service, such as ASR device 141 (FIG. 1A). As described in connection to ASR device 141, the ASR operation returns one or more candidate words or phrases (i.e., the top-N words) most closely matching the utterance. In an embodiment, the ASR system utilized by step 210 comprises a distributed or cloud-based computing service. In an example embodiment reduced to practice the streaming Google Cloud Speech API ASR system was used in step 210 to recognize utterances related to ADLs such as eating, drinking, bathing, dressing, ambulating, and toileting.

In some embodiments of step 210, the ASR operation may also return a confidence value or figure-of-merit corresponding to each of the outputted words or phrases. A figure-of-merit comprises a numerical confidence or probability, which may be represented as a value between 0 and 1, and which represents the closeness of matching (e.g., the inverse of distance) or the likelihood that the ASR-matched word or phrase correctly represents the user's speech utterance. In an embodiment, the confidence value or figure-of-merit may be determined by the ASR system based on an analysis of the digitized information representing the utterance and a database of known words or phrases. For example, if the utterance is the sound wht, then one embodiment of step 210, where N is three, might return the three words: what, wet, wheat. Similarly, where confidence or figure-of-merit values are also provided, then for this example, step 210 may return the values: 0.88, 0.95, 0.15 for the three words respectively.

In some embodiments, the ASR system or device returned words or phrases may be encoded in a hashcode (or hash). For instance, continuing the above example, the hashcodes: 123456, 224455, and 993210 might be returned for: what, wet, and wheat, respectively. Thus, a candidate word or phrase matching an utterance is represented by a hash. FIG. 3B depicts additional examples of a hashcodes (e.g., item 375) and corresponding words (390) and confidence values (e.g., 395). In some embodiment, the hashcode-confidence value pair for each word is determined and provided at step 210.

In some embodiments, the hashcodes may be sorted, such as by an ASCI sort or other sorting operation. Further, in some embodiments, the sorted hashcodes are stored as an N-vector composite code (e.g., a 3-vector code or simple a "3-vector" for embodiments of step 210 that provide three candidate words). For example, in an embodiment of step 210, for each utterance processed by the ASR system or device, the top three likeliest words, phrases or text strings matched by the ASR were provided and stored in a database, such as a SQL database together with the confidence value or match-figure-of-merit for each.

In some embodiments, user settings or parameters may be configured to set the number of words or phrases returned by the ASR operation. For example, in an embodiment, the number of returned words or phrases and corresponding confidence values is three, is between two and five, or is between three and ten. In the example embodiment actually reduced to practice and described in connection to FIGS. 5, 7, and 9A-9C, the top three matches (i.e., N=3) are returned in step 210. In some embodiments, an ASR-related setting may configure the number of words returned based on a confidence value threshold. For example, by setting this threshold to 0.8, then one embodiment may return all words and phrases having a matching confidence value (or figure-of-merit) of at least 0.8. In other embodiments, combinations of these settings may be configured to control the number of candidate words or phrases determined at step 210.

In some embodiments, the confidence values of figures-of-merit are dichotomized. For example, confidence values (or figures-of-merit) near zero and one may be set to zero and one, respectively. (E.g., a confidence value of 0.95 may be set to 1, or a confidence value of 0.15 may be set to 0.) In embodiments where multiple candidate word-confidence-value pairs are returned by the ASR system (or here each returned word is also returned with a confidence value), then those confidence values may be dichotomized to zero or one, based on their values and dichotomization logic. In an embodiment, dichotomization logic specifies a threshold for conditions to set a confidence value to zero or one. (E.g., if the confidence value or probability is greater than 0.9, then set the value to 1). Dichotomization logic also may specify the dichotomization for scenarios with multiple candidate words. For instance, by way of example and without limitation, in an embodiment where the top-3 candidate words and corresponding confidence values are returned by the ASR operation, then dichotomization logic may specify: if all three candidates have a probability greater than 0.9, then set all three values to 1. If two have a probability of greater then 0.6, then set those two to values 1 and set the other value to 0. If only one has a probability of greater than 0.6, then set it to 1 and set the other two values to 0. If none have a probability of greater than 0.3, then set all three values to 0. These are merely example thresholds, which may be adjusted based on the number of words returned, the speaker, the environment, user/operator preference, for example.

In one aspect, dichotomization may convert the floating point values representing confidence or figure-of-merit into binomials (e.g., 0 and 1). An advantage provided from embodiments which utilize dichotomization is that the processing time or complex is reduced and thus the system may be more responsive to the user (i.e., pictogram choices potentially corresponding to the user utterance may be presented sooner). Additionally, training time is reduced.

An example embodiment showing dichotomization is illustratively provided in the table 500 of FIG. 5. With reference to FIG. 5, a table is provided showing a number of sessions or cycles as rows of the table (e.g., rows 501, 502, 506). Each row is identified by a session or trial number in a period column 510, and corresponds to an ASR utterance recognition-pictograms presentation-subsequent user selection of a pictogram. Columns 530, 540, and 550 include dichotomized values of figure-of-merits for each of three candidate words returned by an ASR operation. Column 520 indicates the user's selection of the three choices corresponding to columns 530, 540, and 550. Thus for example, in row 506, the user selected choice 3, identified at item 526, (more accurately, the user selected a pictogram representing a concept corresponding to the third candidate word) which has a dichotomized confidence value of 1, as indicated at item 556. (Row 6 is also shown as item 380 in the example of FIG. 3B. In this example for the pictograms displayed in user interface 370, the user selected choice 3 (pictogram 376) as indicated at item 385, which is the pictogram for a glass of water, and which may correspond to the concept "thirsty." Here, item 386 shows the dichotomization to "1" of the confidence value for the glass of water, 0.95.)

The particular example shown in FIG. 5 corresponds to a relational table from an embodiment actually reduced to practice, and is associated with concepts for drinking. As described above in some embodiments, including this example embodiment, hashcodes representing each of the candidate words or phrases returned from the ASR operation are sorted using an ASCI-sort and formed into a 3-vector.

Returning to FIG. 2A, at step 215 determine concept indicia corresponding to top-N matches. Here "N" corresponds to the number of matches returned by the ASR operation in step 210. Embodiments of step 215 identify and retrieve concepts (which may comprise words) corresponding to the matching candidate words or phrases returned by the ASR operation in step 210. In particular, for each candidate word or phrase one or more corresponding concepts is determined. For instance, continuing the example from step 210, for the word "wet" the concept of "thirsty" may be determined (which may indicate that the speaker is thirsty). In some embodiments, the concepts are retrieved via an inverted index, such as described herein. An index (or inverted index) stores a mapping of items of content, such as words or phrases returned by the ASR system to locations in a database where concepts or related information are stored. In particular an inverted index allows rapid retrieval of information based on a given index item to search on.

As described above, in some embodiments candidate matches are encoded and may be returned form the ASR operation as hashcodes. For example, where the number of words or phrases returned is three (i.e., N=3), the ASR-determined words or phrases may be assembled into a hashcode-sorted 3-vector (step 210), which then may be used to retrieve the previously stored concepts and/or pointers to the associated pictograms from an inverted index. In some embodiments, after an initialization and/or training operation is performed, an ML model (such as an FSM model) may be used with the index to identify concepts corresponding to the candidate words or phrases, such as described above. In other embodiments, or prior to completing initialization or training, no ML model may be used or a default-configured model may be used.

At step 220, determine concept pictograms representing the concepts determined from step 215. Embodiments of step 220 determine the pictograms representing the concepts, which correspond to the candidate words or phrases returned by the ASR operation. In an embodiment, a machine-readable storage repository (such as word/concept pictogram repository 130 in operating environment 100 (FIG. 1A)) containing concept pictograms representing the concepts is retrieved for the top-N indicia. In an embodiment an index, such as an inverted index as described above includes a pointer to a storage location of a pictogram or may include data for displaying the pictogram. As described in connection to FIG. 1A, the pictograms may comprise images that are representative of a concept and may be bitonal (e.g., black and white). Example pictograms are depicted within interface 335 on FIG. 3A and items 372, 374, and 376 on FIG. 3B.

At step 225, present pictograms to the user and receive a user selection of a pictogram. Embodiments of step 225 present a set of pictograms to the user or speaker and receive the user's selection of a pictogram (if any) that best matches the user's intended meaning. In some embodiments of step 225, a set of pictograms is displayed via user interface, such as interface 142 of operating environment 100 (FIG. 1A). Examples of graphical user interfaces depicting pictograms are shown as items 335 of FIG. 3A and 370 of FIG. 3B. In some embodiments, the pictograms are displayed via a touchscreen and user selection is received by the user's touching (e.g., via finger, stylus, or other pointing means) a part of the touchscreen displaying a particular pictogram. Additional details of interfaces suitable for performing step 225 are described in connection to interface 142 of operating environment 100 (FIG. 1A).

In some embodiments, the number of pictograms presented is limited so that a user does not have to scroll or search for a particular pictogram-representation of a concept; for instance in an embodiment between 3 and 5 pictograms may be presented. In some embodiments, the order of the pictograms presented corresponds to the likelihood that the pictogram-represented concept matches the user's intent. For instance, in an embodiment, the pictogram corresponding to the concept that is most likely the user's intent is displayed as the left-most pictogram (or depending on the user's mobility or whether the user is left-handed or right-handed, the pictogram may be presented so that it is easiest for the user to select). A likelihood of the pictogram (or the concept it represents) matching the user's intent may be determined based on the confidence value of a returned ASR word or phrase that corresponds to the concept and/or based on the output of the FSM model (or other ML model) that considers historical information from the user (e.g., historical sessions comprising ASR utterance recognition-pictograms presentation-subsequent user selection of a pictogram).

Embodiments of step 225 also include receiving or acquiring information about the user's selection of a pictogram from the set of presented pictograms. In an embodiment, the user's selection is represented as an integer or number indicating the selected pictogram (or may indicate a hashcode corresponding to a concept represented by the pictogram, such as those described in the example table 500 of FIG. 5). Some embodiments of step 225 receive the user's selection and store the user's selection along with information about the alternative pictograms (or concepts they represent) that were presented but not selected. This information may be used in some embodiments of step 230 for determining (or updating) an ML model, thereby improving the accuracy of these embodiments.

At step 230, determine a finite state machine (FSM) model from M trials of the user's selection and the top alternative concepts corresponding to a user's utterances. Embodiments of step 230 determine an FSM model from data about a number of trials or sessions of ASR utterance recognition-pictograms presentation-subsequent user selection of a pictogram as well as information about the alternative concepts represented by the pictograms presented to the user, which the user did not select. The FSM model captures information about the transitions that accumulate with repeated utterances and selections. As described in an embodiment of step 225, information about the user's selection and alternative pictograms not selected may be stored and used for generating an ML model, such as the FSM model generated in step 230. In some embodiments of step 230, the trials comprises sessions from past utterances of a user received at step 208, and information about historical selections of pictograms representing concepts corresponding to those utterances, is used to determine the FSM model. In an embodiment, the number of trials is between two hundred and approximately twenty thousand sessions of ASR utterance recognition-pictograms presentation-subsequent user selection of a pictogram. Although it is contemplated that fewer trials may be used, the resulting model will be less accurate. Similarly, there may be little benefit to requiring more than twenty-thousand trials before using the FSM model. Embodiments of method 200 continue to utilize and update the model based on subsequent user utterances. In an example embodiment actually reduced to practice and described in connection to FIGS. 5, 7, and 9A-9C, fifteen thousand trials were utilized.

Figure 6:
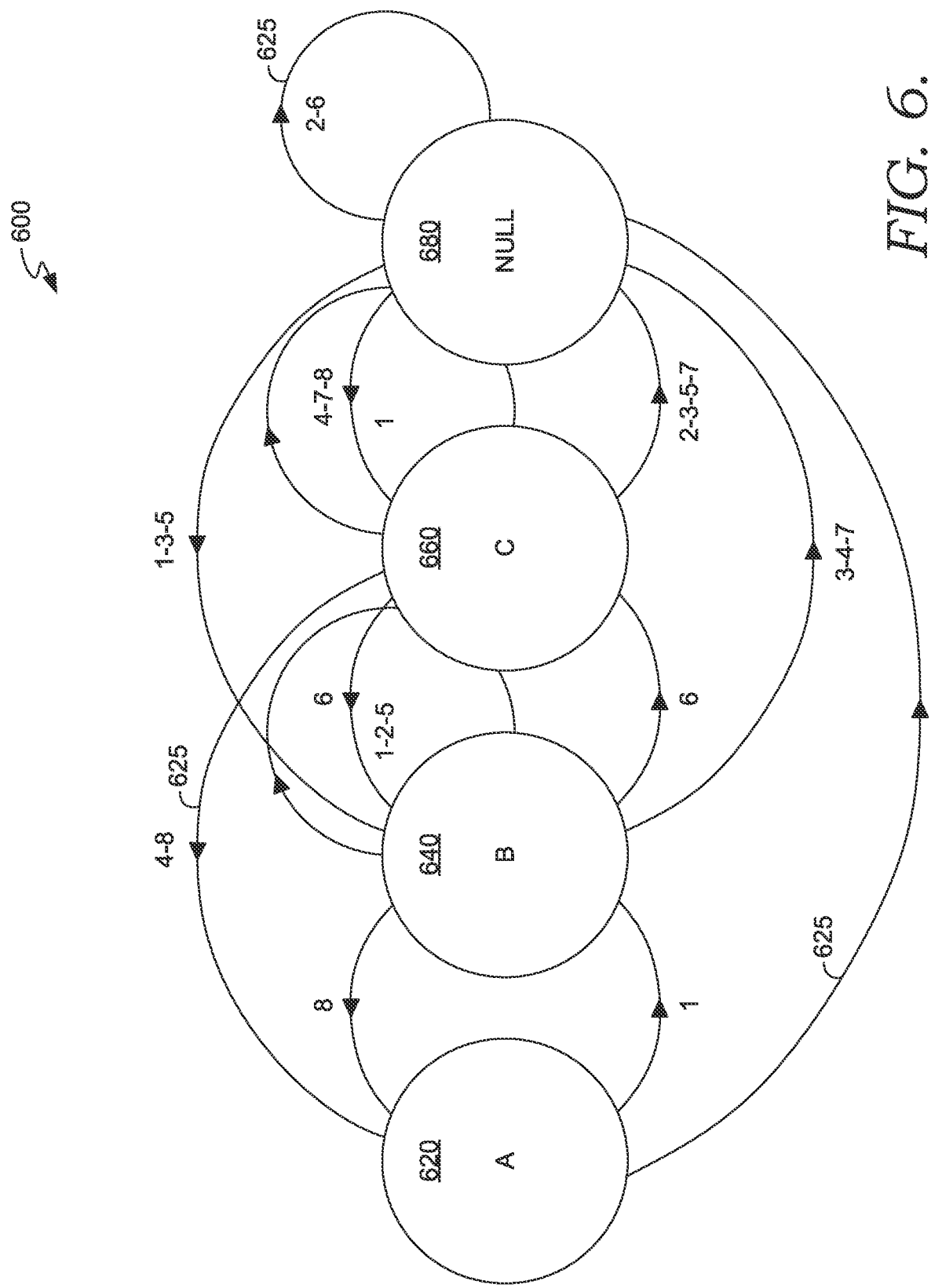
FIG. 6 depicts aspects of a finite state machine model, which may be used in an embodiment of the disclosure.

In an embodiment, the FSM model is implemented as a transition matrix which includes information about each state and probabilities of traversing to a next state. Some embodiments of step 230 utilize the GA (genetic algorithm) or datafsm packages of the R-system as shown in the example computer program routine of FIGS. 9A-9C. Additional details of the GA or datafsm packages are described in connection to computation services 126 of operating environment 100 (FIG. 1A). For example, in the embodiment of the computer program provided in FIG. 9A-9C, an FSM model is generated (as a transition matrix) using the GA genetic algorithm. In particular, optimum action-vectors (represented by the model) are determined and represent the accrued set of utterance-pictogram' pairs from among the large set of candidate alternatives. In some embodiments, a plurality of FSM models are determined, which may vary by context, utterance, or topic, which may be determined from an utterance or previous utterances. An example depicting aspects of an FSM model is illustratively provided in FIG. 6. With reference to FIG. 6, a portion of an example FSM model is provided and referred to generally as FSM model 600. FSM model 600 includes four states: A, B, C, and Null, which are shown at items 620, 640, 660, and 680 respectively. From each state 620, 640, 660, and 680, one or more arcs 625 are shown representing the transitions.

Returning to FIG. 2A, at step 235, the FSM determined in step 230 is stored. Information about the ASR-processed utterances, such as the hashcode representations of the candidate words or phrases and corresponding concept indicia may also be stored in step 235. In particular, where this information is newly encountered by the system (i.e., for new or additional utterances are received and processed, which were not previously processed when determining the FSM model). This information may be stored in an data store such as data store 207, which may be embodied as storage 121 of operating environment 100 (FIG. 1A). Some embodiments of method 200 are iterative and include updating the FSM model with subsequent future utterances received by a user. In an embodiment, the FSM is structurally represented as a transition matrix and thus may be stored as a relational database file structure. The FSM model may be accessed and applied to future utterances by the user, such as at step 240.

At step 240, apply the FSM model to the current utterance. Embodiments of step 240 use the FSM model determined (or updated) in step 230 for determining a likely corresponding concept from a the current utterance, received at step 202. In particular, once method 200 has initialized or trained the FSM model, then in response to the user's current or subsequent utterances and the ASR recognition output of candidate words, the FSM model may produce a probability-rank-ordered or confidence-rank-ordered list of corresponding concepts based on the immediately prior state of the FSM.

At step 245, determine pictograms corresponding to the top concepts identified in step 240 and receive the pictograms from storage. In an embodiment of step 240 and 245, the top-N matches returned from the ASR operation are sorted as an N-vector in hashcode order and with the FSM model, used to determine the top corresponding concepts and pictograms representing these concepts. In an embodiment of step 240 and 245, hashcodes representing the top N matches from the ASR operation are sorted (e.g., by using ASCI-sort) and used to traverse the FSM to determine an FSM state, from which then a rank-order listing of concepts is determined. Some embodiments of step 245 may be performed as described in connection with embodiments of step 220.

At step 250, present pictograms to the user and receive a user selection of a pictogram. Embodiments of step 225 present a set of pictograms to the user or speaker and receive the user's selection of a pictogram (if any) that best matches the user's intended meaning. Embodiments of step 250 may be carried out as described in connection with embodiments of step 225.

At step 255, store information about the user's selection and the rank-ordered alternative concepts (represented by the other pictograms that were not selected). In particular, information about the ASR-processed utterance, such as the hashcode representations of the candidate words or phrases, information about the corresponding concepts or pictogram representations, and the user's selection may be stored. This information may be stored in an data store such as data store 207, which may be embodied as storage 121 of operating environment 100 (FIG. 1A). Embodiments of step 255 may store the results and alternatives in an inverted index and/or in a log, where it may be used (e.g., by a genetic algorithm) in a subsequent iteration of method 200 to update the FSM model.

At step 260 perform an action corresponding to the user's selected pictogram. In an embodiment of step 260, the action performed comprises digitally synthesizing text-to-speech for the concept corresponding to the pictogram, and playing it via a speaker or other acoustic transducer such that can be heard by the speaker or a human caregiver, either nearby or remotely. In one embodiment, the action comprises displaying word(s) that describe the concept, such as displaying "I am thirsty" for the concept thirsty. In an embodiment, the audio or displayed words describing the concept may be provided to the user-speaker via interface 142. In some embodiments, the action comprises, by way of example and without limitation, initiating a communication (e.g., calling someone), emitting a notification, causing an action to occur in the user-speaker's environment (e.g., changing the channel on a television, turning on/off the lights, opening a door, adjusting the thermostat), or a similar action) corresponding to the concept represented by the pictogram selected by the user.

Some embodiments of the steps of method 200 may be carried out using the example computer program routine depicted in FIGS. 9A-9C.

With reference now to FIG. 2B, method 201 is shown as another example embodiment of a method for processing speech to determine an action or concept corresponding to a speaker's intent. Method 201 depicts an example application of an embodiment of this disclosure that utilized an already initialized FSM model on a current utterance. In contrast, method 200 included steps for creating the FSM model. Accordingly method 201 begins at step 275, wherein a user's speech is acquired and digitized. Some embodiments of step 201 may be performed as described in step 202 of method 200.

At step 280, perform an ASR operation on the digitized speech utterance. Embodiments of step 280 perform an ASR operation and return a set of top-N candidate words or phrases most likely matching the utterance. Some embodiments of step 280 may be performed as described in step 210 of method 200. At step 285, one or more concepts corresponding to the candidate words or phrases returned by the ASR operation are determined and pictograms representing the concepts are determined and retrieved. Some embodiments of step 285 are performed as described in connection to steps 240 and 245 of method 200.

At step 290, the set (or a subset) of pictograms determined in step 285 are presented to a user for selection and the user's selection is received. Some embodiments of step 290 may be carried out as described in connection to step 250 of method 200. At step 295, perform an action corresponding to the user's selected pictogram. Some embodiments of step 295 may be carried out as described in connection to step 260 of method 200.

Figure 3A:
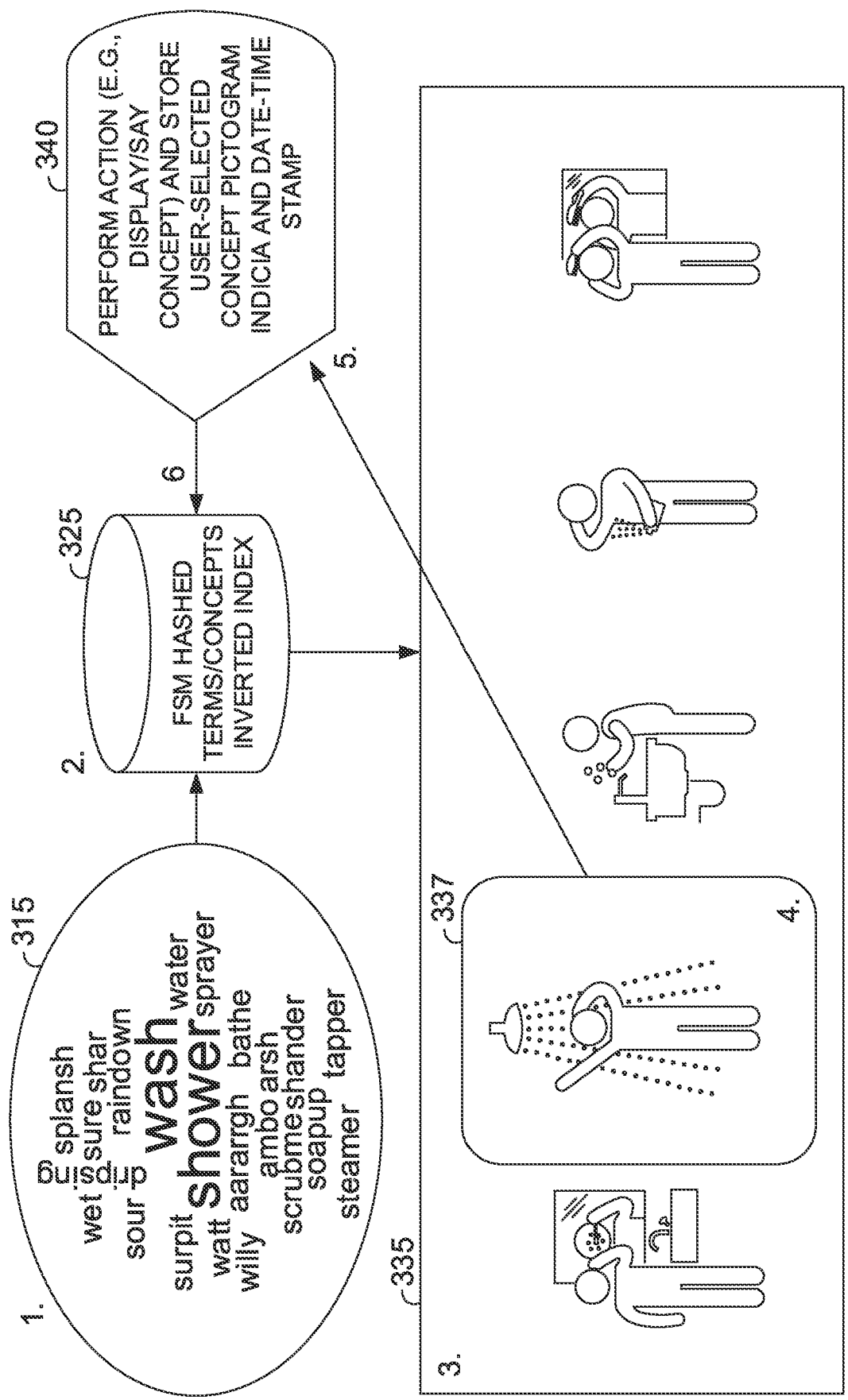
FIGS. 3A-3B depict aspects of example embodiments of a tool for assisting disabled speakers, in accordance with an embodiment of the disclosure.
Figure 3B:
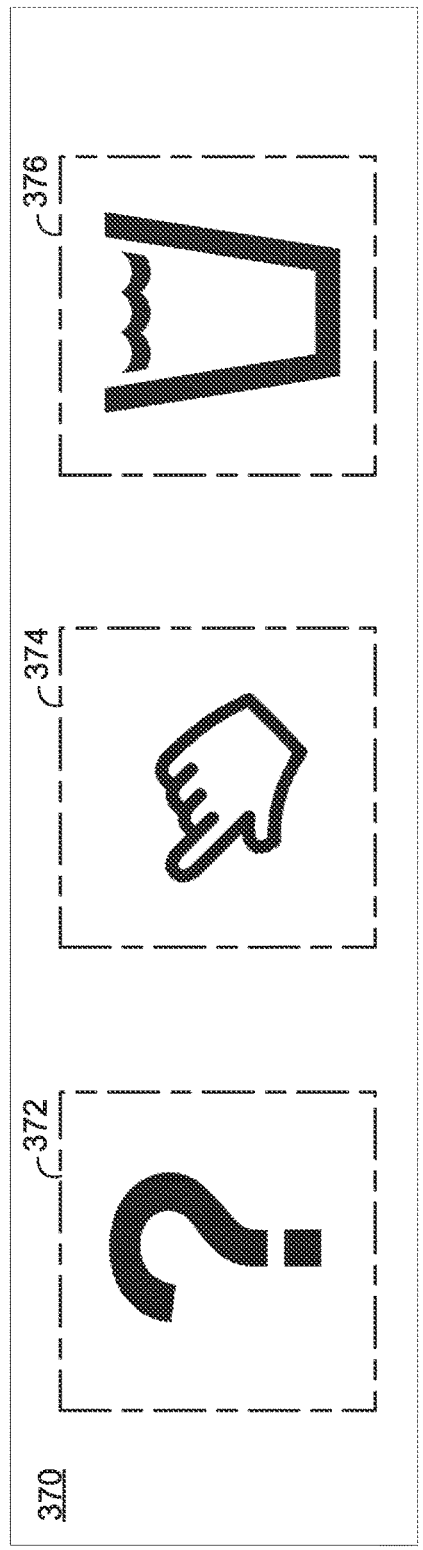
Figures 4A, 4B:
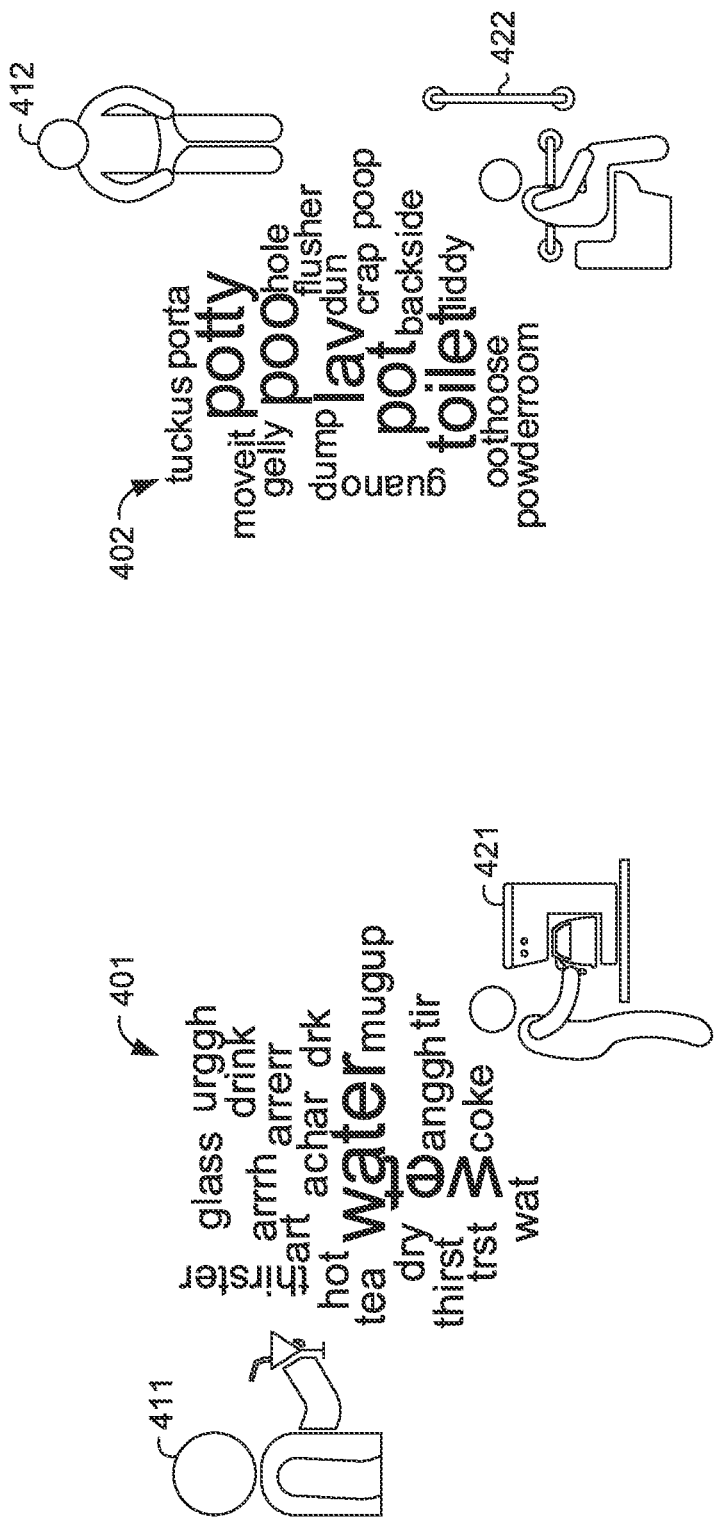
FIGS. 4A-4B depict word clouds representations of example utterances by a speaker and example pictograms representing concepts corresponding to the utterances, in accordance with an embodiment of the disclosure.
Figure 8:
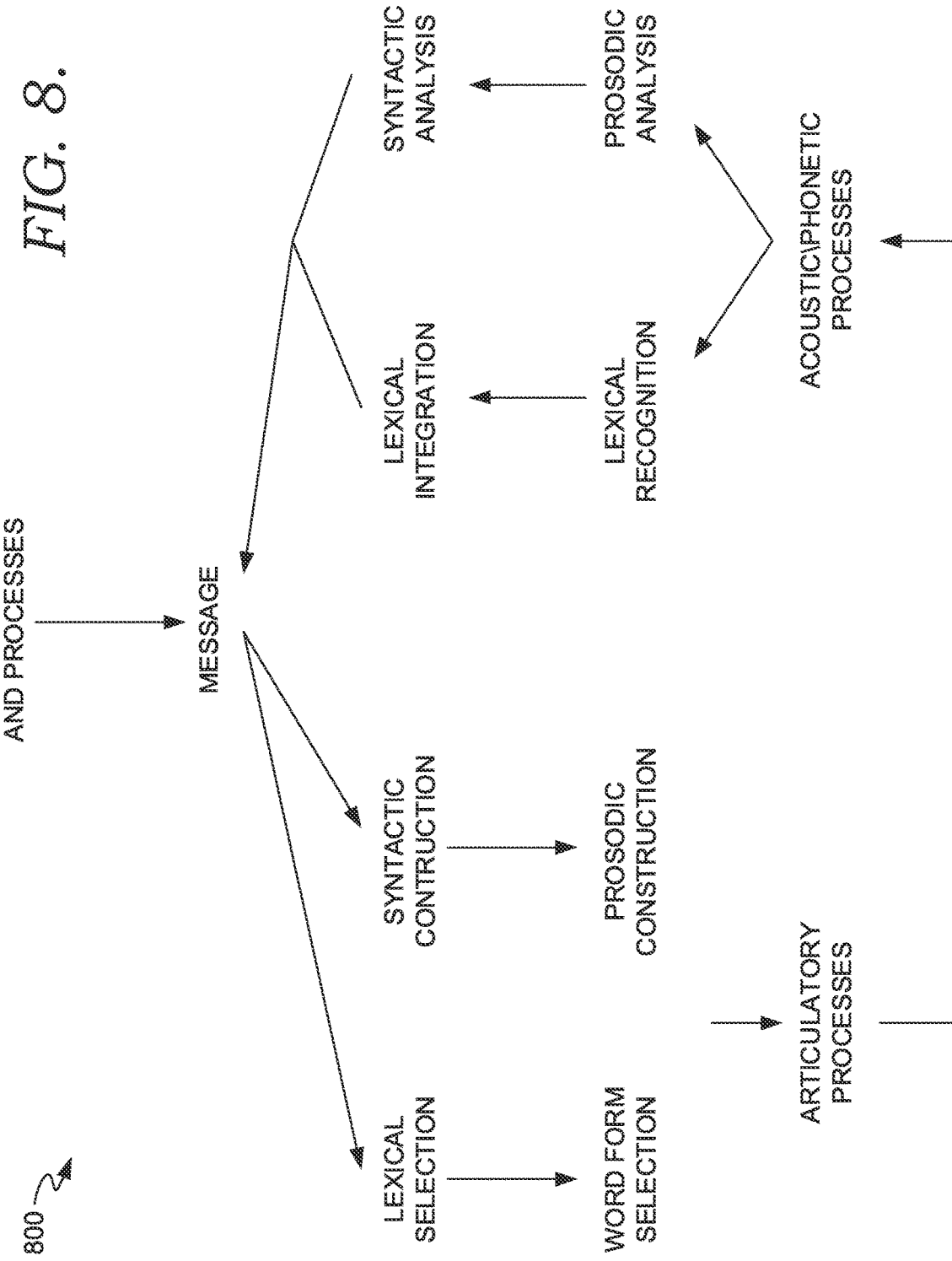
FIG. 8 depicts a directed graph showing an aspect of a linguistic processing cycle.

Turning now to FIG. 3A aspects are depicted of an example embodiment of a tool for assisting impaired speakers. In this example, the speaker desires to shower or bathe. A word-cloud 315 is shown comprising a set of words corresponding to utterances by a speaker indicating the speaker's desire (to shower). The words shown in word-cloud 315 may be detected from speaker utterances by an ASR operation, such as described in method 200. The size of a particular word in word-cloud 315 indicates the frequency with which a particular word was detected from an utterance. For example, the words shower and bathe were most frequently detected by this particular speaker, but other words, such as wet, splansh, or dripsing, for example, were also detected. FIGS. 4A and 4B depict additional examples of word-clouds and corresponding pictograms representing concepts (e.g., drinking and toilet) corresponding to the words shown in each word cloud. (FIG. 8, which is provided for reference, depicts aspects of the linguistic processing cycle performed by a speaker from conceiving or having a desire or intent, and forming an acoustic utterance expressing a message attempting to indicate the desire or intent.)

Continuing with FIG. 3A, next at item 325, an FSM model and inverted index is utilized to identify concepts corresponding to the ASR-detected utterances. From these concepts, a set of pictograms representing the concepts may be provided to the user via user interface 335. A user selects a particular pictogram corresponding to his or her desire. Here, pictogram 337 is selected by the user, which corresponds to the concept of showering. In some embodiments, when the user selects a particular pictogram, it is highlighted. At 340, an action is performed based the user's selection, such as displaying or saying the concept (i.e., synthesizing text-to-speech or playing back an audio recording of the concept). The user selection is stored back at item 325 along with a date-time stamp of the time of the selection. In some embodiments, date-time information about a user selection may be used as contextual information to more accurately infer user intent (e.g., in the morning's the utterance "wet" corresponds to shower, but in the evenings it corresponds to "I want a cocktail"). Date-time information also may be utilized to determine longitudinal patterns or timeseries of user utterances and corresponding selections, which may be used for improving the model or for improving performance of the system. For example, in an embodiment, the date-time information of a selection may be used to determine staleness or freshness of user utterance and corresponding intent. Some utterances, for example, may be pruned or de-emphasized (i.e., ranked lower) if they are less frequently uttered or no longer uttered at all.

Figure 10:
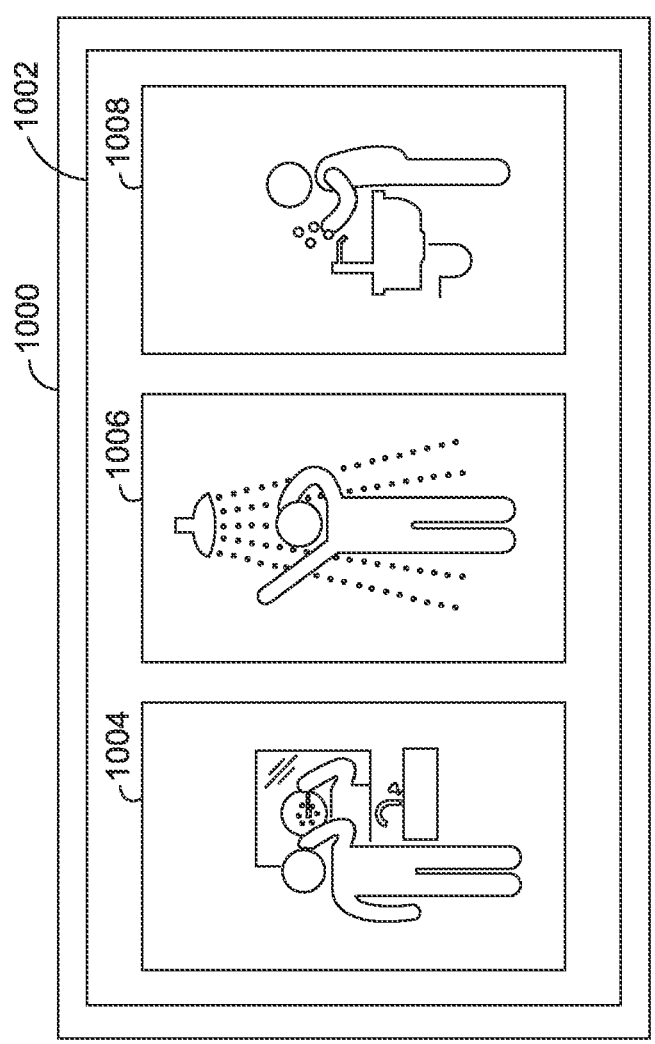
FIG. 10 illustrates an example user device having and electronic display.

Turning now to FIG. 10, which is an illustrated example of a user device 1000. User device 1000 may include a user interface for visually conveying information, such as electronic display 1002. As previously described, the user device 1000 may be a mobile device, such as a tablet, smartphone, smartwatch, and the like. The electronic display 1002 may be utilized to visually present a rendered GUI.

In the example provided by FIG. 10, the rendered GUI visually presented by the electronic display 1002 includes pictograms 1004, 1006, and 1008. The pictograms 1004, 1006, and 1008 are examples and may be determined and presented using methods previously described. For example, each of the pictograms 1004, 1006, and 1008 may be determined from an utterance of a user. For example, from the user's utterance, a candidate word may be determined, and from the candidate word, a concept maybe determined. Using the concept, the pictogram may be retrieve from an indexed set of pictograms.

In the example provided by FIG. 10, the pictograms 1004, 1006, and 1008 are arranged so that pictogram 1004 is presented on the far left of the electronic display 1002, and pictogram 1008 is presented on the far right of electronic display 1002, while pictogram 1006 is arranged between pictogram 1004 and pictogram 1008. As an example, the arrangement of pictograms 1004, 1006, and 1008 may be determined based on a rank-order of the concepts that correspond to the determined candidate words. That is, pictogram 1004 could have the highest rank that corresponds to the utterance, while pictogram 1006 has a rank lower than pictogram 1004 and pictogram 1008 has a rank lower than pictogram 1006. Of course this is merely an example and the arrangement could be inverse with the highest rank arranged on the far right. In some embodiments, a user setting may determine the arrangement.

Additionally, one example might be to arrange one or more pictograms based on the user's anatomical mobility. In an example previously described, if a person is right-hand dominate, the pictogram corresponding to the highest rank for the utterance may be arranged in the GUI so that it is visually presented on the right side. Similarly if the person is left-hand dominate, the pictogram corresponding to the highest rank may be arranged on the left. It will be appreciated that any number of pictograms may be presented, and that only three are illustrated in FIG. 10 for simplicity in describing the technology.

Based on the pictograms rendered in the GUI, a selection of a pictogram may be received. For example, this selection may represent a user's intent corresponding to the speech utterance. Context information, such as date-time information, associated with the utterance may be determined and may be indexed with the selected pictogram and/or indexed with the concept represented by the selected pictogram for future concept determination. In some cases, the context information may be indexed with an unselected pictogram and/or the concept represented by the unselected pictogram for future concept determination.

Thus, for example, the pictogram that is selected from a first GUI may illustrate a concept, and the pictogram and concept may be stored with contextual information determined from a speech utterance. The contextual information and the concept represented by the selected pictogram may be used to train a machine learned model that is used in future concept determination. That is, for example, a second GUI may be generated having a plurality of pictograms that are determined using the machine-learning model that was trained using the selection from the first GUI. In this example, each subsequent GUI may be rendered with one or more pictograms that are more likely to portray a concept that is intended by the user making the speech utterance.

Example Reduction to Practice

With reference to FIGS. 5, 7, 9A-9C and continuing reference to method 200 of FIG. 2A and FIGS. 1A and 1B, an example is provided of an embodiment of the disclosure actually reduced to practice. Here, computer system 120 running the Linux operating system (129) was utilized with the open-source statistical software package R, and the R modules GA and datafsm (Computation services 126). This embodiment used the computer program routine provided in FIGS. 9A-9C.

For this example embodiment, informed consent was obtained from a cohort of individuals having stable mixed aphasia with dysarthria whose duration exceeded eighteen months, including primary progressive aphasia (PPA). PPA is a form of frontotemporal dementia that is characterized by progressive language impairment without other notable cognitive impairment. In this example reduction to practice, two subtypes of PPA (semantic dementia (SD) and progressive nonfluent aphasia (PNFA)) were encountered. SD is typically marked by fluent but empty speech, obvious word-finding difficulties, but comparatively preserved grammar abilities. In contrast, PNFA is characterized by halting and sometimes a grammatic speech, reduced syntactic complexity, and relatively spared single-word comprehension.

In contract to conventional approaches for classifying PPA subtypes from ASR transcripts, which for example are unable to include any syntactic complexity, our ADL-oriented implementation included connected speech, temporal sequencing, and other routine complexities involved in dining, drinking, bathing, toileting, grooming, dressing, and ambulation. All participants were native speakers of English.

The AQ subtest of the Western Aphasia Battery-Refined (WAB-R) was administered to participants, yielding scores between 72.2 and 92.8 for study participants. To elicit a sample of narrative speech unrelated to ADLs, we further asked participants to tell the well-known story of Cinderella. Participants were given a wordless picture book to remind them of the story; then the book was removed and they were asked to tell the story in their own words.

The streaming Google Cloud Speech API ASR system was used to recognize utterances related to ADLs, including eating, drinking, bathing, dressing, ambulating, and toileting. While embodiments of the technologies described herein contemplate multiple-choice from among a plurality of an arbitrarily large number of selections of pictograms, in practice users prefer embodiments having from 2 to 5 selections from which the user may choose. In this example implementation actually reduced to practice, three possible pictogram selections were presented in response to each ASR recognized utterance. For each recognized utterance, the "top 3" likeliest words or text-strings matched by the ASR were stored in, and retrieved from, an SQL database, together with the probability or match-figure-of-merit for each. Each was hash-encoded and mapped to one or more related concepts, which in turn were associated with a bitonal pictogram (JPEG rendering from vector line-art) suitable for display on a tablet or smartphone device. A sample of 15,000 such utterances and pictogram selections from each speaker was utilized for construction of a finite-state machine (FSM) model, using open-source FSM discovery software running in parallelized mode on a 4-core Linux computer having 32 GB of main memory. Additionally, an open-source genetic algorithm was used to determine the optimum action-vector representing the accrued set of 'utterance-pictogram' pairs from among the large set of candidate solutions, and the resulting FSM model stored on persistent mass storage for later retrieval and application. The 3-vector of hashcodes of the "top-3" ASR matches for each utterance was stored on the same system using an inverted index file structure. Subsequently when "repeat" occurrences strongly resembling a given utterance class were encountered by the ASR system, the hashcodes of the "top-3" ASR-determined words or phrases were assembled into a hashcode-sorted 3-vector, which was then used to retrieve the previously stored concepts and pointers to the associated pictograms from the inverted index. These, in turn, were displayed on the user's mobile device and the user selected by touch-screen user-interface from among the three pictograms the one choice that most closely approximated their then-current intended meaning. The hashcode corresponding to the user's choice was then stored in the database, enabling longitudinal sequences of the user's selecting particular pictograms to be analyzed statistically for determining the accuracy of the ASR system's recognition of the user's utterances and for purposes of ongoing improvement of the FSM model for retrieving the likeliest concepts and the corresponding pictograms most likely to be assented-to by the user, based on their historical selection patterns.

Figure 7:
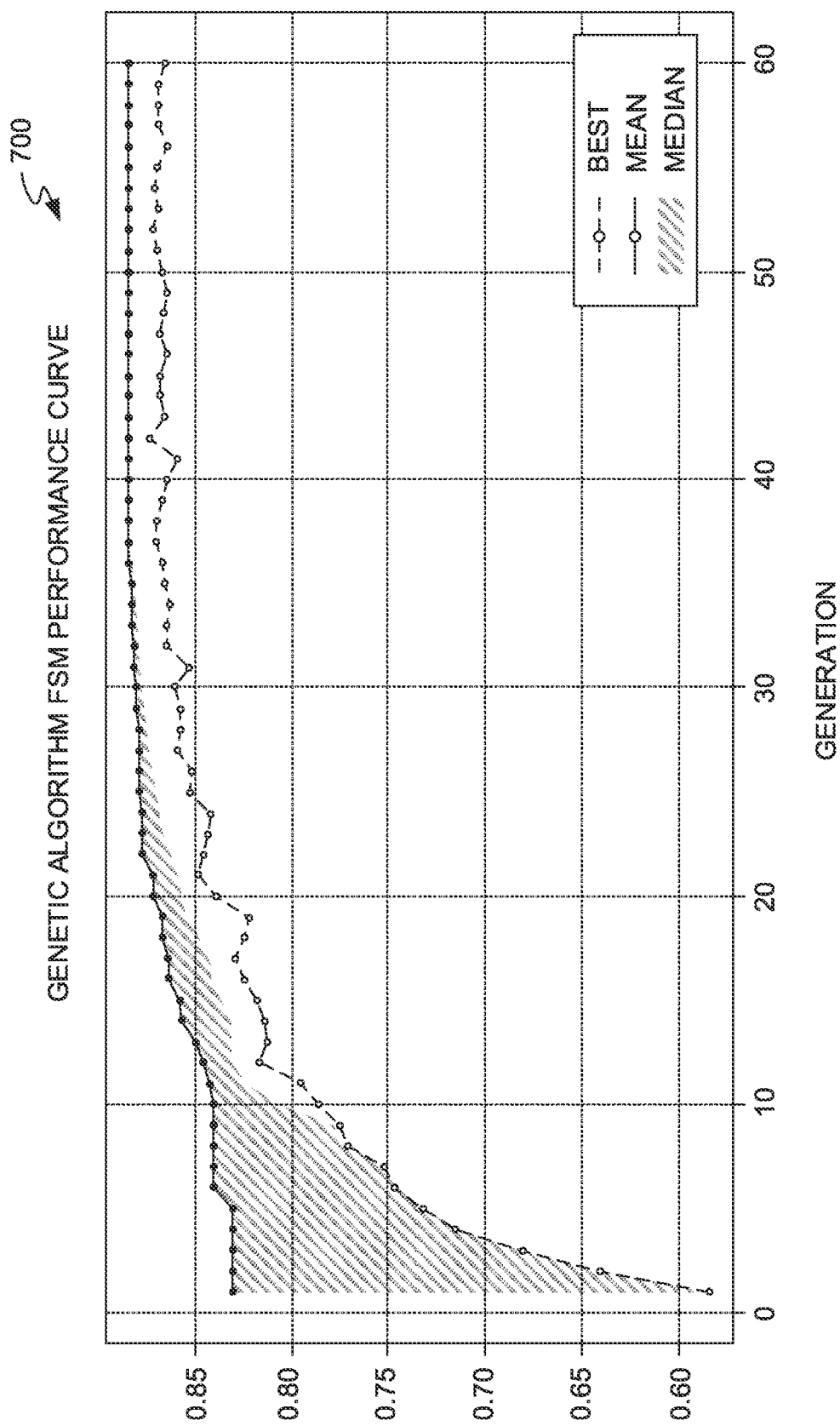
FIG. 7 shows the statistical performance of an embodiment of the disclosure that utilizes a genetic algorithm to determine a finite state machine with mutations.

FIG. 7 shows statistical performance of the example embodiment reduced to practice, using a genetic algorithm determined FSM model. As can be observed in the performance curve, after enough mutations generations (reflected in the number of generations, since each generation introduces some mutation), the performance is about 85% accurate for this data.

Some example embodiments of the technology described herein include:

Embodiment 1: A system for assisting an impaired speaker comprising: a user interface configured to display images and receive a selection of an image by the speaker; an acoustic sensor configured to detect and digitize a sound; an ASR system configured to detect an utterance from digitized sound information and perform an ASR operation on the detected utterance; one or more processors; and memory storing one or more pictograms and computer-useable instructions that, when executed by the one or more processors, implement a method comprising: acquiring, using the acoustic sensor, digitized sound information of a speech utterance by the speaker; performing, using the ASR system, an operation on the digitized sound information to determine a set of candidate words or phrases likely matching the utterance; determining a set of concepts corresponding to the set of candidate words or phrases; for each concept, retrieving a pictogram representing the concept from a location in the computer memory, thereby forming a set of pictograms; displaying the set of pictograms using the user interface; receiving an indication of a selection of a pictogram by the speaker; based on the selection, performing an action corresponding to the selection.

Embodiment 2: Embodiment 1, wherein an FSM model is utilized to determine the set of concepts corresponding to the set of candidate words or phrases.

Embodiment 3: Any of Embodiments 1-2, wherein an inverted index is used to identify concepts based on the candidate word or phrases.

Embodiment 4: Any of Embodiments 1-3, wherein an inverted index is also used to identify concepts based on the candidate word or phrases.

Embodiment 5: Any of Embodiments 1-4, wherein the FSM model returns a rank-ordered list of concepts.

Embodiment 6: Any of Embodiments 1-5, wherein the FSM model is determined using a genetic or evolutionary algorithm.

Embodiment 7: Any of Embodiments 1-6, wherein the set of pictograms is between two and five pictograms in size.

Embodiment 8: Any of Embodiments 1-7

Embodiment 9: Any of Embodiments 1-8, wherein the user interface is further configured to provide emit acoustic data to the speaker, and wherein the action performed comprises emitting an audio indication of the concept corresponding to the selected pictogram.

Embodiment 10: Any of Embodiments 1-9, wherein the user interface is further configured to provide emit acoustic data and wherein the action performed comprises performing text-to-speech synthesis of the concept corresponding to the speaker's selection and emitting the synthesized sound.

Embodiment 11: Any of Embodiments 1-10, wherein action performed corresponding to the speaker's selection comprises displaying the concept represented by the selected pictogram on the user interface.

Embodiment 12: Any of Embodiments 1-11, wherein the ASR operation determines a confidence value for each candidate word or phrase.

Embodiment 13: Any of Embodiments 1-12, wherein each candidate word or phrase determined by the ASR operation is hash-encoded.

Embodiment 14: Any of Embodiments 1-13, wherein the hashcodes representing the candidate words or phrases are sorted and formed into a composite vector.

Embodiment 15: Any of Embodiments 1-14, wherein the user's selection and the alternative pictograms are utilized to update the FSM model.

Embodiment 16: A method comprising: receiving a digitized speech utterance from a human speaker; past ASR-recognized utterances of the speaker are retrieved and ASR is performed, returning top-N matches and match figure-of-merit for each; indicia are identified for each word/concept corresponding to the top-N ASR-recognized matches; a machine-readable storage repository containing word/concept pictograms for word/concept candidates is retrieved for the top-N indicia, and the pictograms are displayed via a computer graphical user interface to the user, enabling the user to select which pictogram (if any) best matches user's intended meaning; from the combination of predictive top-N probe concepts and the user's selections are determined a finite state machine FSM model from top-N alternatives and the selection made by the user from M trials; wherein the resulting FSM model is stored in persistent machine-readable storage and subsequently said FSM model is retrieved and applied when new utterances from said user are received and processed by the ASR system, yielding a new set of top-N matches and their numerical figure-of-merit metrics; wherein the top-N probe concepts are hash encoded and sorted and stored in an N-vector inverted index; the FSM model is applied to the then-current utterance and its top-N matches, hashcoded and sorted to form an N-vector; the N-vector is then used to retrieve one or more extant records of the same N-vector, one or more concept-related pictograms associated with the N-vector's components, and the user's previously stored historical selection from among these pictograms; wherein the words/phrases and associated concept pictograms are retrieved from machine-readable storage and presented to user via computerized user interface equipped with a touch-screen user-input capability and the user's selection of which pictogram (if any) best matches user's intended meaning is acquired by the user's touching the device approximately in the area where their selected pictogram is displayed; and wherein the currently-selected pictogram indicia results are stored, and an action (such as digitally synthesizing text-to-speech for the concept or word and playing it via a speaker or other acoustic transducer that can be heard by the user or a human caregiver, either nearby or remotely) corresponding to user selection is performed.

Embodiment 17: Embodiment 16, wherein N is between 3 and 10; wherein M is between 200 and 20,000; and wherein the figure-of-merit metrics comprise probabilities between 0.0 and 1.0.

Embodiment 18: Any of Embodiments 16-17, wherein the ASR system is streaming, distributed, and/or cloud-based.

Embodiment 19: Any of Embodiments 16-18, wherein the figure-of-merit that is returned by the ASR system for each word or phrase detected and matched is a numerical confidence or probability with a value between 0 and 1 representing the closeness of matching (inverse of distance) or the likelihood that the ASR-matched word or phrase correctly represents the user's speech utterance.

Embodiment 20: Any of Embodiments 16-19, wherein concept- or word-associated pictograms associated with ASR-detected utterances are designed so as to represent the concept or word and stored as digitized images in machine-readable form (such as PNG, JPEG, GIF formats, or vector graphics formats) suitable for rendering on a computer-based display device.

Embodiment 21: Any of Embodiments 16-20, wherein the user's device is a tablet computer or a smartphone.

Embodiment 22: Any of Embodiments 16-21, wherein the device's user interface includes a touch screen capable of displaying a set comprised of a plurality of said pictograms on a graphical display with members of the set are arranged in a defined geometrical orientation with respect to each other.

Embodiment 23: Any of Embodiments 16-22, wherein a pointing or touch gesture designating selection initiated by the user is received by the touch screen subsystem and in which the approximate location on the touch screen of the user's touching/pointing (via finger, stylus, or other pointing means) is detected and associated with the pictogram selected from among the plurality of pictograms displayed.

Embodiment 24: Any of Embodiments 16-23, wherein each concept or word selected is stored in an inverted index data structure in persistent machine-readable storage, and the inverted index stores a mapping from items of content, such as words or concepts recognized by the ASR subsystem, to locations in a database where the items and data associated with them occur, the purpose of an inverted index being to allow rapid retrieval of one or more entities that reference a given indexed item.

Embodiment 25: Any of Embodiments 16-24, wherein discovery of a finite state machine (FSM) model of serial "ASR utterance recognition-pictograms presentation-user selection of pictogram" cycles is performed by a genetic or evolutionary algorithm.

Embodiment 26: Any of Embodiments 16-25, wherein the FSM model produces in response to the user's subsequent utterances and ASR recognition output a probability-rank-ordered or confidence-rank-ordered list of probe words or concepts based on the immediate prior state of the FSM.

Embodiment 27: Any of Embodiments 16-26, wherein a plurality of FSM models are directed to different topical or time-of-day or situational contexts that alter the likelihoods of intentions and meanings underlying the user's speech acts.

Embodiment 28: Any of Embodiments 16-27, wherein a plurality of FSM models are directed to different thematic activities or narrative sequences, such as arise in performance of different activities of daily living (ADLs) and wherein the likelihoods of intentions and meanings underlying the user's speech acts are altered.

Embodiment 29: Any of Embodiments 16-28, wherein the FSM (or the set of multiple context-specific FSMs) is (are) retrained on a periodic or ongoing basis from longitudinal samples of the user's utterances, ASR output, and user selections of pictograms presented.

Embodiment 30: Any of Embodiments 16-28, wherein an advisory interpretive message regarding the joint significance of the changes, if any, is electronically emitted to the human user.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method, comprising:
   acquiring digitized sound information associated with a speech utterance;
   performing digital speech processing on the digitized sound information to identify candidate words or phrases in a first language likely matching the speech utterance;
   determining, at one or more processors, a plurality of candidate concepts based on the candidate words or phrases and based further on a machine-learning electronic model, wherein:
   (a) the machine-learning electronic model is trained based on (i) one or more historical speech utterances of a user in the first language, the one or more historical speech utterances comprising a speech disorder, a speech impairment, a speech impediment, or any combination thereof, and (ii) contextual information of the one or more historical speech utterances, the contextual information including time of day information, user activity information, user activity patterns or routines, user schedule information, or any combination thereof, and
   (b) applying the machine-learning electronic model to data associated with the candidate words or phrases generates information indicating the plurality of candidate concepts;
   presenting, via the one or more processors and an electronic user interface, a plurality of pictograms associated with the plurality of candidate concepts;
   receiving, via the electronic user interface, a selection of a pictogram from the plurality of pictograms, wherein the pictogram is indicative of an intended meaning of the speech utterance; and
   based on the selection, performing an action corresponding to the selection, wherein the action produces in the first language the intended meaning of the speech utterance.

2. The method of claim 1, wherein the determining comprises identifying a first candidate concept, of the plurality of candidate concepts, that corresponds to at least a subset of the candidate words or phrases.

3. The method of claim 2, wherein the determining further comprises accessing information, associated with one or more historical speech utterances corresponding to a communication disorder, stored at a computer memory associated with the one or more processors.

4. The method of claim 3, further comprising generating a ranked list of concepts, from the plurality of candidate concepts, based on a likelihood of each concept in the list representing the speech utterance.

5. The method of claim 4, further comprising: for each concept within the ranked list, retrieving a pictogram representing the concept from a location in the computer memory.

6. The method of claim 1, wherein the presenting comprises displaying the pictograms based on a user's anatomical mobility and a likelihood of each of the pictograms representing, in the first language, the speech utterance in the first language.

7. The method of claim 1, wherein the action comprises one or more of: emitting an audio indication of a concept corresponding to the selected pictogram, performing textto-speech synthesis of a concept corresponding to the selection and emitting a synthesized sound, or displaying the concept represented by the selected pictogram on the electronic user interface.

8. One or more non-transitory media having instruction that, when executed by one or more processors, cause the one or more processers to facilitate a plurality of operations, the operations comprising:
acquiring digitized sound information associated with a speech utterance;
performing digital speech processing on the digitized sound information to identify candidate words or phrases in a first language likely matching the speech utterance;
determining, at the one or more processors, a plurality of candidate concepts based on the candidate words or phrases and based further on a machine-learning electronic model, wherein:
(a) the machine-learning electronic model is trained based on (i) one or more historical speech utterances of a user in the first language, the one or more historical speech utterances comprising a speech disorder, a speech impairment, a speech impediment, or any combination thereof, and (ii) contextual information of the one or more historical speech utterances, the contextual information including time of day information, user activity information, user activity patterns or routines, user schedule information, or any combination thereof, and
(b) applying the machine-learning electronic model to data associated with the candidate words or phrases generates information indicating the plurality of candidate concepts;
presenting, via the one or more processors and an electronic user interface, a plurality of pictograms associated with the plurality of candidate concepts;
receiving, via the electronic user interface, a selection of a pictogram from the plurality of pictograms, wherein the pictogram is indicative of an intended meaning of the speech utterance; and
based on the selection, performing an action corresponding to the selection, wherein the action produces in the first language the intended meaning of the speech utterance.

9. The one or more non-transitory media of claim 8, wherein the determining comprises identifying a first candidate concept, of the plurality of candidate concepts, that corresponds to at least a subset of the candidate words or phrases, and wherein the plurality of candidate concepts includes the identified first candidate concept.

10. The one or more non-transitory media of claim 9, wherein the determining further comprises accessing information, associated with one or more historical speech utterances corresponding to a communication disorder, stored at a computer memory associated with the one or more processors.

11. The one or more non-transitory media of claim 10, wherein the operations further comprise generating a ranked list of concepts, from the plurality of candidate concepts, based on a likelihood of each concept in the list representing the speech utterance.

12. The one or more non-transitory media of claim 11, wherein the operations further comprise: for each concept within the ranked list, retrieving a pictogram representing the concept from a location in the computer memory.

13. The one or more non-transitory media of claim 8, wherein the presenting comprises displaying the pictograms based on a user's anatomical mobility and a likelihood of each of the pictograms representing the speech utterance.

14. The one or more non-transitory media of claim 8, wherein the action comprises one or more of: emitting an audio indication of a concept corresponding to the selected pictogram, performing text-to-speech synthesis of a concept corresponding to the selection and emitting a synthesized sound, or displaying the concept represented by the selected pictogram on the electronic user interface.

15. A system having one or more processors configured to facilitate a plurality of operations, the operations comprising:
acquiring digitized sound information associated with a speech utterance;
performing digital speech processing on the digitized sound information to identify candidate words or phrases in a first language likely matching the speech utterance;
determining, at the one or more processors, a plurality of candidate concepts based on the candidate words or phrases and based further on a machine-learning electronic model, wherein:
(a) the machine-learning electronic model is trained based on (i) one or more historical speech utterances of a user in the first language, the one or more historical speech utterances comprising a speech disorder, a speech impairment, a speech impediment, or any combination thereof, and (ii) contextual information of the one or more historical speech utterances, the contextual information including time of day information, user activity information, user activity patterns or routines, user schedule information, or any combination thereof, and
(b) applying the machine-learning electronic model to data associated with the candidate words or phrases generates information indicating the plurality of candidate concepts;
presenting, via the one or more processors and an electronic user interface, a plurality of pictograms associated with the plurality of candidate concepts;
receiving, via the electronic user interface, a selection of a pictogram from the plurality of pictograms, wherein the pictogram is indicative of an intended meaning of the speech utterance; and
based on the selection, performing an action corresponding to the selection, wherein the action produces in the first language the intended meaning of the speech utterance.

16. The system of claim 15, wherein the determining comprises identifying a first candidate concept, of the plurality of candidate concepts, that corresponds to at least a subset of the candidate words or phrases.

17. The system of claim 16, wherein the determining further comprises accessing information, associated with one or more historical speech utterances corresponding to a communication disorder, stored at a computer memory associated with the one or more processors.

18. The system of claim 17, wherein the operations further comprise generating a ranked list of concepts, from the plurality of candidate concepts, based on a likelihood of each concept in the list representing the speech utterance.

19. The system of claim 18, wherein the operations further comprise: for each concept within the ranked list, retrieving a pictogram representing the concept from a location in the computer memory.

20. The system of claim 15, wherein the presenting comprises displaying the pictograms based on a user's anatomical mobility and a likelihood of each of the pictograms representing the speech utterance.

21. The system of claim 15, wherein the action comprises one or more of: emitting an audio indication of a concept corresponding to the selected pictogram, performing text-to-speech synthesis of a concept corresponding to the selection and emitting a synthesized sound, or displaying the concept represented by the selected pictogram on the electronic user interface.

22. The method of claim 1, wherein the speech utterance corresponds to an utterance, and wherein the candidate word instances and the candidate phrase instances are identified via digital speech processing and based on prior utterances by the speaker.

23. The method of claim 1, wherein the machine-learning electronic model is based on a genetic algorithm or an evolutionary algorithm.

24. The method of claim 1, wherein the machine-learning electronic model is associated with a finite state machine (FSM).

25. The method of claim 24, wherein the FSM is configured to facilitate generation of a rank-ordered list that includes the plurality of candidate concepts.

26. The one or more non-transitory media of claim 8, wherein the determining further comprises accessing particular information, associated with one or more historical speech utterances corresponding to at least one communication disorder selected from a group comprising a particular speech disorder, a particular speech impairment, and a particular speech impediment, stored at a computer memory associated with the one or more processors.

\* \* \* \* \*